(12) United States Patent
Chung et al.

(10) Patent No.: US 10,618,874 B2
(45) Date of Patent: Apr. 14, 2020

(54) COMPOUNDS, COSMETIC COMPOSITION AND PHARMACEUTICAL COMPOSITION COMPRISING THE SAME

(71) Applicant: INCOSPHARM CORPORATION, Daejeon (KR)

(72) Inventors: Hwa-Jee Chung, Daejeon (KR); Myung Ho Kor, Daejeon (KR); Heung Jae Kim, Daejeon (KR); Sung Woo Kim, Daejeon (KR); Seok Jeong Yoon, Daejeon (KR); Ju Yeon Jung, Sejong-si (KR); Ka Young Shin, Daejeon (KR); Se Kyoo Jeong, Daejeon (KR); Kee Don Park, Daejeon (KR)

(73) Assignee: INCOSPHARM CORPORATION, Daejeon (KR)

( * ) Notice: Subject to any disclaimer, the term of this patent is extended or adjusted under 35 U.S.C. 154(b) by 0 days.

(21) Appl. No.: 16/445,116

(22) Filed: Jun. 18, 2019

(65) Prior Publication Data

US 2019/0382340 A1 Dec. 19, 2019

(30) Foreign Application Priority Data

Jun. 18, 2018 (KR) .................. 10-2018-0069587
May 28, 2019 (KR) .................. 10-2019-0062620

(51) Int. Cl.
*C07D 207/16* (2006.01)
*A61Q 19/02* (2006.01)
*A61P 17/00* (2006.01)

(52) U.S. Cl.
CPC ............ *C07D 207/16* (2013.01); *A61P 17/00* (2018.01); *A61Q 19/02* (2013.01)

(58) Field of Classification Search
CPC .................................................. C07D 207/16
See application file for complete search history.

(56) References Cited

PUBLICATIONS

CAS Registry Entry No. 2226415-22-9, which entered STN on Jun. 5, 2018 (Year: 2018).*
CAS Registry Entry No. 2226415-23-0, which entered STN on Jun. 5, 2018 (Year: 2018).*
CAS Registry Entry No. 2226415-24-1, which entered STN on Jun. 5, 2018 (Year: 2018).*
CAS Registry Entry No. 2226415-25-2, which entered STN on Jun. 5, 2018 (Year: 2018).*
Ando et al. "Possible involvement of proteolytic degradation of tyrosinase in the regulatory effect of fatty acids on melanogenesis", Journal of Lipid Research, vol. 40, pp. 1312-1316 (1999).
Hearing et al. "Minireview: Mammalian Tyrosinase—The Critical Regulatory Control Point in Melanocyte Pigmentation", Int. J. Biochem, vol. 19, No. 12, pp. 1141-1147 (1987).
Hung et al. "Autophagy protects neuron from Aβ-induced cytotoxicity, Autophagy", vol. 5, Issue 4, pp. 502-510 (2009).
Kim et al. "Amyloidogenic peptide oligomer accumulation in autophagy-deficient β cells induces diabetes", The Journal of Clinical Investigation, vol. 124, No. 8, pp. 3311-3324 (Aug. 2014).
Qi et al. "The Role of Chaperone-Mediated Autophagy in Huntingtin Degradation", PLOS ONE, vol. 7, Issue 10, pp. 1-16 (Oct. 2012).
Seiberg et al. "The Protease-Activated Receptor 2 Regulates Pigmentation via Keratinocyte-Melanocyte Interactions", Experimental Cell Research, 254, pp. 25-32 (2000).

* cited by examiner

*Primary Examiner* — Matthew P Coughlin
(74) *Attorney, Agent, or Firm* — Knobbe Martens Olson & Bear LLP

(57) ABSTRACT

Disclosed is a novel compound, and a cosmetic composition for whitening and a pharmaceutical composition for preventing and treating a melanin hyperpigmentation disorder by activating autophagy to induce melanosome degradation and also by effectively inhibiting endocytosis of keratinocytes to interfere melanosome transfer into keratinocytes, thereby expressing an excellent effect on improvement, prevention, and treatment of a hyperpigmentation disorder induced from melanin.

21 Claims, 8 Drawing Sheets

COMPOUNDS, COSMETIC COMPOSITION AND PHARMACEUTICAL COMPOSITION COMPRISING THE SAME

CROSS-REFERENCE TO RELATED APPLICATIONS

This application claims priority under 35 U.S.C. § 119 to Korean Patent Application No. 10-2018-0069587 AND 10-2019-0062620, filed on Jun. 18, 2018 and May 28, 2019, respectively, in the Korean Intellectual Property Office, the disclosure of which is incorporated herein by reference in its entirety.

TECHNICAL FIELD

The following disclosure relates to a novel compound, and a cosmetic composition and a pharmaceutical composition including the same, and more particularly, to a novel compound which induces melanosome degradation by autophagy activation and inhibits endocytosis into keratinocytes, and a cosmetic composition for skin whitening and a pharmaceutical composition for preventing and treating a melanin hyperpigmentation disorder, including the same.

BACKGROUND

Skin color is largely determined by a melanin amount, hemoglobin, carotene, and the like, and among them, melanin plays the most important role. Melanin determines the skin color of a person and also serves to protect the skin; however, when melanin is excessively produced in the skin by changes in external environment such as overexposure to ultraviolet light, air pollution, stress, and inflammation, pigmentation occurs, resulting in dark skin color or causing spots or freckles. Among the external stimulating factors, ultraviolet light is the strongest stimulus of melanin biosynthesis and may affect various processes related to melanin production. That is, ultraviolet light acts as a main factor for inducing overproduction of melanin by promoting activity of melanocytes which are melanin-producing cells, promoting secretion of a melanocyte-stimulating hormone, promoting oxidation of melanin, promoting tyrosinase activity, and the like.

RELATED ART DOCUMENTS

Non-Patent Document

Hung et al. Autophagy, 2009, 5, 4, 502-510
Hearing & Jimenez, Int J Biochem, 1987, 19(12), 1141-7
Funasaka et al. J Lipid Res. 1999, July; 40(7), 1312-6
Qi et al. PLOS one, 2012, 7, 10, e46834
Xilouri et al. Brain, 2013, 136, 2130-2146
Kim et al. The Journal of Clinical Investigation, 2014, 124, 8, 3311-3324
Seiberg et al. Experimental Cell Research, 2000, 254, 25-32

SUMMARY

An embodiment of the present invention is directed to providing a novel compound which may induce melanosome degradation by autophagy activation and a pharmaceutically acceptable salt thereof.

Another embodiment of the present invention is directed to providing a novel compound which may decrease endocytosis of melanosomes by PAR-2 activation inhibition and a pharmaceutically acceptable salt thereof.

Another embodiment of the present invention is directed to providing a cosmetic composition for skin whitening including the compound or the pharmaceutically acceptable salt thereof as an effective component.

Still another embodiment of the present invention is directed to providing a pharmaceutical composition for improving or treating a melanin hyperpigmentation disorder including the compound or the pharmaceutically acceptable salt thereof as an effective component.

In one general aspect, a compound represented by the following Chemical Formula 1 which may induce melanosome degradation by autophagy activation and a pharmaceutically acceptable salt thereof are provided:

[Chemical Formula 1]

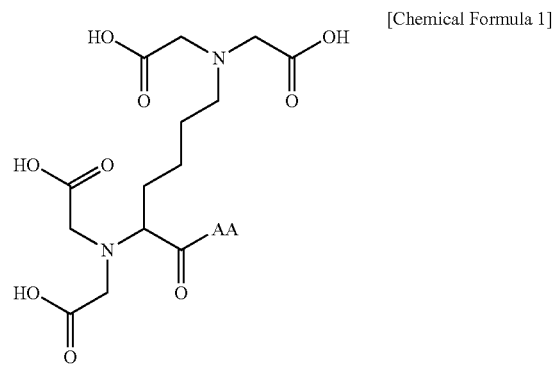

wherein

AA is an amino acid residue containing unsubstituted or substituted proline.

In Chemical Formula 1, AA may be an amino acid residue containing proline which is unsubstituted or substituted with one or more substituents selected from the group consisting of hydroxy, $C_{1-10}$ alkoxy, $C_{1-10}$ alkylcarbonyl, carboxy, and the like.

Chemical Formula 1 may be a compound represented by the following Chemical Formula 2 or a pharmaceutically acceptable salt thereof:

[Chemical Formula 2]

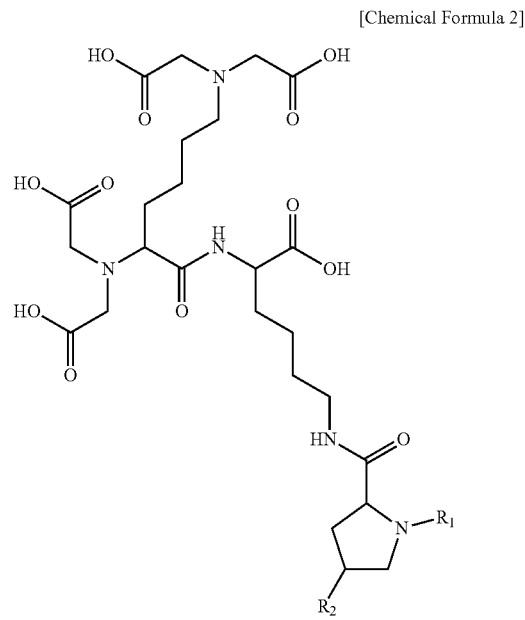

wherein

R$_1$ is C$_{1-10}$ alkylcarbonyl; and

R$_2$ is hydrogen, hydroxy, C$_{1-10}$ alkoxy, C$_{1-10}$ alkylcarbonyl, or carboxy.

Chemical Formula 1 may be a compound represented by the following Chemical Formula 3 or a pharmaceutically acceptable salt thereof:

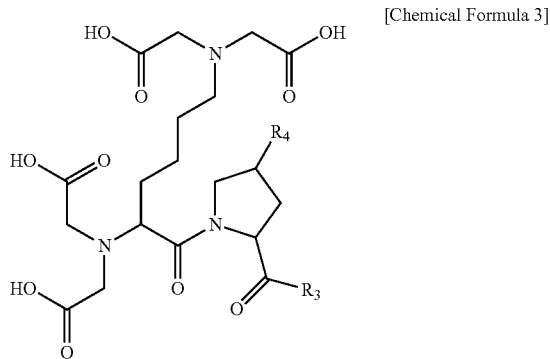

[Chemical Formula 3]

wherein

R$_3$ is hydroxy or C$_{1-10}$ alkyl; and

R$_4$ is hydrogen, hydroxy, C$_{1-10}$ alkoxy, C$_{1-10}$ alkylcarbonyl, or carboxy.

In another general aspect, a cosmetic composition for skin whitening includes the compound represented by Chemical Formula 1 or the pharmaceutically acceptable salt thereof as an effective component.

In the cosmetic composition for skin whitening, the effective component may be selected from the compound represented by Chemical Formula 2 or the pharmaceutically acceptable salt thereof (A).

In the cosmetic composition for skin whitening, the effective component may be selected from the compound represented by Chemical Formula 3 or the pharmaceutically acceptable salt thereof (B).

In the cosmetic composition for skin whitening, the effective component may be a mixture of the compound represented by Chemical Formula 2 or the pharmaceutically acceptable salt thereof (A) and the compound represented by Chemical Formula 3 or the pharmaceutically acceptable salt thereof (B).

In the cosmetic composition for skin whitening, the effective component may be a mixture mixed at a weight ratio (A:B) of 1:0.1 to 1:1.

In the cosmetic composition for skin whitening, the effective component may be included at 0.0001 to 10 wt %, based on the total weight of the composition.

In still another general aspect, a pharmaceutical composition for improving or treating a melanin hyperpigmentation disorder includes the compound represented by Chemical Formula 1 or the pharmaceutically acceptable salt thereof as an effective component.

In the pharmaceutical composition for improving or treating a melanin hyperpigmentation disorder, the effective component may be selected from the compound represented by Chemical Formula 2 or the pharmaceutically acceptable salt thereof (A').

In the pharmaceutical composition for improving or treating a melanin hyperpigmentation disorder, the effective component may be selected from the compound represented by Chemical Formula 3 or the pharmaceutically acceptable salt thereof (B').

In the pharmaceutical composition for improving or treating a melanin hyperpigmentation disorder, the effective component may be a mixture of the compound represented by Chemical Formula 2 or the pharmaceutically acceptable salt thereof (A') and the compound represented by Chemical Formula 3 or the pharmaceutically acceptable salt thereof (B').

In the pharmaceutical composition for improving or treating a melanin hyperpigmentation disorder, the effective component may be a mixture mixed at a weight ratio (A':B') of 1:0.1 to 1:1.

In the pharmaceutical composition for improving or treating a melanin hyperpigmentation disorder, the melanin hyperpigmentation disorder may be selected from the group consisting of freckles, senile plaque, liver spots, chloasma, brown or black spots, sunlight pigmented spots, cyanic melasma, hyperpigmentation after using drugs, chloasma gravidarum, hyperpigmentation after inflammation, and the like.

In the pharmaceutical composition for improving or treating a melanin hyperpigmentation disorder, the effective component may be included at 0.0001 to 10 wt %, based on the total weight of the composition.

Other features and aspects will be apparent from the following detailed description, the drawings, and the claims.

DETAILED DESCRIPTION OF EMBODIMENTS

Figure 1:
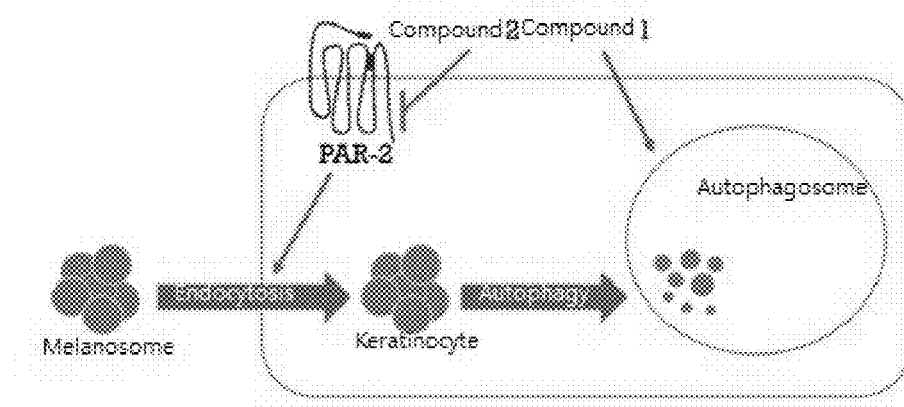
FIG. 1 is a drawing schematizing a mechanism in which a pigmentation process of the keratinocyte is inhibited.

Hereinafter, the novel compound, and the cosmetic composition and the pharmaceutical composition including the same according to embodiments of the present invention will be described, but technical terms and scientific terms used herein have the general meaning understood by those skilled in the art to which the present invention pertains unless otherwise defined, and a description for the known function and configuration obscuring the present invention will be omitted in the following description.

In the present specification, the terms, "alkyl", "alkoxy", and other substituents including the "alkyl" part includes all forms of a straight chain and a branched chain. In addition, alkyl, alkoxy, and the like according to embodiments of the present invention are preferentially those having 1 to 10 carbon atoms in a straight chain form or those having a straight chain form having the number of carbons, but those having 11 to 30 carbon atoms are also an embodiment of the present invention, of course.

In the present specification, "alkylcarbonyl" refers to *—C(=O)alkyl, in which the alkyl follows the definition described above.

In the present specification, "a pharmaceutically acceptable salt thereof" is prepared using common technology known in the art, and includes salts derived from pharmaceutically acceptable inorganic acids, organic acids, or bases. An example of the inorganic acid or inorganic acid may include hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, trifluoroacetic acid, citric acid, methanesulfonic acid, formic acid, benzoic acid, malonic acid, naphthalene-2-sulfonic acid, benzenesulfonic acid, or the like. In addition, an example of the base may include alkali metals such as potassium and sodium; alkaline earth metals such as magnesium; ammonium; or the like.

In the present specification, "improvement" refers to all actions to alleviate a state, make a state better, or change a state advantageously by applying the composition according to embodiments of the present invention.

In addition, a singular form used in the present specification may be intended to also include a plural form, unless otherwise indicated in the context.

In addition, units used in the present specification without particular mention is based on weights, and as an example, a unit of % or ratio refers to a wt % or a weight ratio.

In addition, the numerical range used in the present specification includes all values within the range including the lower limit and the upper limit, increments logically derived in a form and span in a defined range, all double limited values, and all possible combinations of the upper limit and the lower limit in the numerical range defined in different forms.

In addition, in the present specification, the expression, "comprise" is an open-ended description having a meaning equivalent to the expression such as "provided", "contain", "have", or "is/are characterized", and does not exclude elements, materials, or processes which are not further listed.

The biosynthesis of melanin proceeds by the action of various genes such as tyrosinase, tyrosinase related protein 1 (TRP-1), tyrosinase related protein 2 (TRP-2), and Pmel17, and enzymes corresponding thereto. In addition, it is affected by an interaction of cytokines such as alpha-melanocyte-stimulating hormone (α-MSH), IL-1, tumor necrosis factor-alpha (TNF-α), granulocyte-macrophage colony-stimulating factor (GM-CSF).

Most whitening materials are those inhibiting tyrosinase activity. However, some whitening materials inhibiting tyrosinase activity cause safety problems such as leukoplakia, irritation, and an allergic reaction. As an example, hydroxyquinone which inhibits tyrosinase most effectively has a side effect of killing melanocytes. Thus, there is a strong demand for the development of whitening materials that control the endocytosis of melanosomes into keratinocytes, without affecting tyrosinase expression and a melanin content in melanocytes.

Autophagy refers to a mechanism to degrade aged or damaged intracellular components and organelles when intracellular energy source is depleted or intracellular stress factors are excessively generated, thereby regenerating energy and removing damaged components. As aging proceeds or as aging is accelerated, intracellular autophagy activation is rapidly decreased. When autophagy is inhibited, aged mitochondria, misfolded proteins, and the like are excessively accumulated in cells, resulting in increase of free radicals or oxidative stress in cells, and as a result, gene fragments are produced by apoptosis. These gene fragments stimulate melanocytes to induce maturation of melanosomes and transport into keratinoctyes.

By activating autophagy, intracellular aged components and organelles such as modified proteins and lipids, damaged mitochondria, and the like are degraded and recycled, apoptosis is prevented by activation of antioxidant proteins, thereby eventually providing an healthy environment where cells may remove the maturation factors of melanosomes. Besides, several recent reports have found that autophagy activation regulates lightening of skin color as well as 3D artificial skin color.

In addition, a protease-activated receptor 2 (PAR-2) expressed in keratinocytes is related to endocytosis of melanosomes into keratinocytes, through which pigmentation may be regulated. That is, activation of PAR-2 by trypsin induces pigmentation, which may cause hyperpigmentation or a nonuniform skin tone.

Thus, the present inventors invented a novel compound which effectively degrades melanosomes in keratinocytes by autophagy activation to effectively inhibit skin pigmentation and also promotes PAR-2 inhibition to effectively inhibit melanosome transfer into keratinocytes, and a use of it for whitening.

The present inventors repeated the study on whitening materials, and devised a novel compound which may effectively induce melanosome degradation by autophagy activation. The compound according to embodiments of the present invention has excellent autophagy activation ability and is expected to be actively utilized in improvement, prevention, and treatment of a melanin hyperpigmentation disorder.

Specifically, the compound according to embodiments of the present invention increases expression of an autophagy activation-related protein, which induces melanosome degradation. Thus, production of melanosome may be effectively inhibited. Accordingly, a composition including the compound as an effective component may exhibit an excellent effect on improvement, prevention, and treatment of a melanin hyperpigmentation disorder as well as a skin whitening effect.

At the same time, the compound according to embodiments of the present invention inhibits activation of protease-activated receptor 2 (PAR-2) and effectively inhibits endocytosis of keratinocytes, thereby effectively preventing transfer of melanosomes into keratinocytes.

Hereinafter, the present disclosure will be described in detail.

The compound according to an embodiment of the present invention may be represented by the following Chemical Formula 1 and a pharmaceutically acceptable salt thereof.

[Chemical Formula 1]

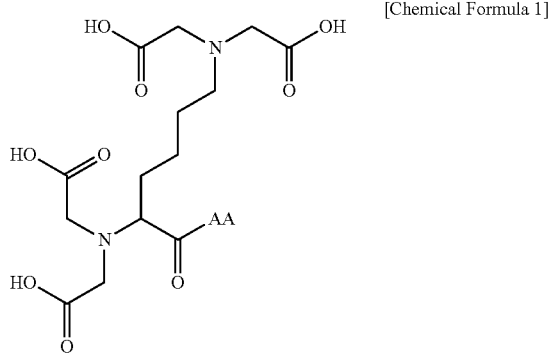

wherein

AA is an amino acid residue containing unsubstituted or substituted proline.

The compound represented by Chemical Formula 1 and the pharmaceutically acceptable salt thereof activate intracellular autophagy and induce melanosome degradation simultaneously, and effectively inhibit expression of melanogenesis associated transcription factor (MITF). In addition, the compound and the pharmaceutically acceptable salt thereof inhibit maturation of, inhibit endocytosis in keratinocytes, and implement a surprising whitening effect. That is, the compound represented by Chemical Formula 1 according to embodiments of the present invention may be usefully utilized as a whitening material having an autophagy activation function.

Intracellular autophagy activation actively occurs in tissues and cells of young people, but as aging proceeds, an expression level of intracellular autophagy-related proteins is rapidly decreased, thereby a degree of autophagy activation is rapidly decreased. Thus, intracellular aged proteins, lipids and mitochondria are not timely removed so that a cellular aging phenomenon rapidly occurs. According to embodiments of the present invention, autophagy activation allows aging of each cell, each tissue, and each individual to be basically inhibited and various diseases caused by the aging to be prevented, improved, and treated.

In addition, activation of autophagy improves aged cell viability through removal of intracellular harmful proteins and organelles, and moreover, and is also closely associated with a lifespan of each individual.

Thus, the compound represented by Chemical Formula 1 or the pharmaceutically acceptable salt thereof inhibits maturation of melanosomes in melanin cells caused by various factors and acts on prevention and treatment of a melanin hyperpigmentation disorder more usefully.

In Chemical Formula 1, AA may be an amino acid residue containing proline which is unsubstituted or substituted with one or more substituents selected from the group consisting of hydroxy, $C_{1-10}$ alkoxy, $C_{1-10}$ alkylcarbonyl, and carboxy.

As an example, in Chemical Formula 1, AA may be an amino acid residue containing proline bonded by an amide bonding. Herein, the proline and the amino acid residue other than proline may be unsubstituted or substituted with the above-descried substituents. In addition, in the amino acid residue, two or more amino acids containing proline is bonded by an amide bonding.

As an example, in Chemical Formula 1, AA may be an amino acid residue containing proline bonded by an amide bonding, in which the amino acid residue may contain one or more selected from the group consisting of Asn, Gln, Lys, and the like having two N-terminals.

As an example, in Chemical Formula 1, AA may be an amino acid residue directly bonded with proline which is unsubstituted or substituted with the above-descried substituents.

The compound according to an embodiment of the present invention may be a compound represented by the following Chemical Formula 2:

[Chemical Formula 2]

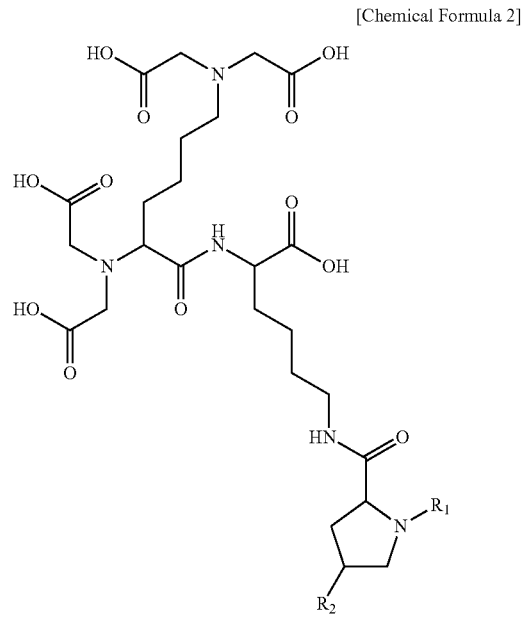

wherein $R_1$ is $C_{1-10}$ alkylcarbonyl; and $R_2$ is hydrogen, hydroxy, $C_{1-10}$ alkoxy, $C_{1-10}$ alkylcarbonyl, or carboxy.

Since the compound represented by Chemical Formula 2 shows excellence in a melanosome degradation effect by autophagy activation, in the present specification, the compound may refer to a melanosome degradation inducing compound by autophagy activation.

As an example, in Chemical Formula 2, $R_1$ may be $C_{1-4}$ alkylcarbonyl; and $R_2$ may be hydrogen, hydroxy, or $C_{1-4}$ alkoxy.

As an example, in Chemical Formula 2, $R_1$ may be straight chain $C_{1-4}$ alkylcarbonyl; and $R_2$ may be hydrogen or hydroxy.

As an example, in Chemical Formula 2, $R_1$ may be $C_{1-2}$ alkylcarbonyl; and $R_2$ may be hydrogen or hydroxy.

In addition, the compound represented by Chemical Formula contains one or more chiral asymmetric carbon atoms. Accordingly, the compound represented by Chemical Formula 2 may be present in a racemic body and an optically active form. That is, the diastereomers and enantiomers of the compound represented by Chemical Formula 2 are all included in the scope of the present invention.

The compound according to an embodiment of the present invention may be a compound represented by the following Chemical Formula 3:

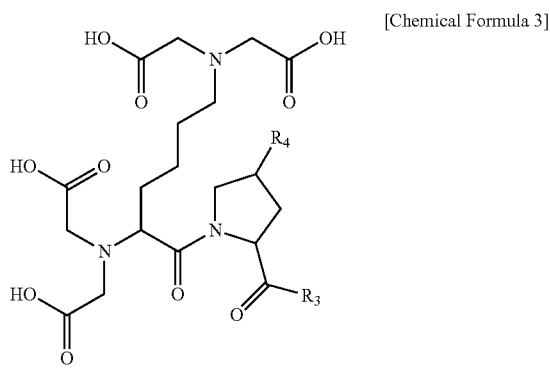

[Chemical Formula 3]

wherein $R_3$ is hydroxy or $C_{1-10}$ alkyl; and $R_4$ is hydrogen, hydroxy, $C_{1-10}$ alkoxy, $C_{1-10}$ alkylcarbonyl, or carboxy.

Since the compound represented by Chemical Formula 3 may effectively inhibit transfer of melanosome into keratinocytes by endocytosis inhibition, in the present specification, the compound may refer to a melanosome transfer inhibition inducing compound by endocytosis inhibition.

As an example, in Chemical Formula 3, $R_3$ may be hydroxy or $C_{1-4}$ alkyl; and $R_4$ may be hydrogen, hydroxy, or $C_{1-4}$ alkoxy.

As an example, in Chemical Formula 3, $R_3$ may be hydroxy or straight chain $C_{1-4}$ alkyl; and $R_4$ may be hydrogen, hydroxy, or straight chain $C_{1-4}$ alkoxy.

As an example, in Chemical Formula 3, $R_3$ may be hydroxy or $C_{1-2}$ alkyl; and $R_4$ may be hydrogen or hydroxy.

In addition, the compound represented by Chemical Formula contains one or more chiral asymmetric carbon atoms. Accordingly, the compound represented by Chemical Formula 3 may be present in a racemic body and an optically active form. That is, the diastereomers and enantiomers of the compound represented by Chemical Formula 3 are all included in the scope of the present invention.

Hereinafter, the use of the present invention will be described in detail.

The use of an embodiment of the present invention may be a cosmetic composition for whitening.

The cosmetic composition for whitening according to an embodiment of the present invention may include the compound represented by Chemical Formula 1 or the pharmaceutically acceptable salt thereof as an effective component.

The compound represented by Chemical Formula 1 or the pharmaceutically acceptable salt thereof expresses a whitening effect even in a very low concentration range (for example, 1 M) without causing cytotoxicity within a range of concentration showing activity. In addition, the compound represented by Chemical Formula 1 or the pharmaceutically acceptable salt thereof does not reduce stability or storability of a formulation even in the case of being formulated into a common cosmetic composition.

The cosmetic composition for whitening according to an embodiment of the present invention may include the compound represented by Chemical Formula 2 or the pharmaceutically acceptable salt thereof (A) as an effective component. Herein, (A) may be one or a mixture of two or more.

The cosmetic composition for whitening according to an embodiment of the present invention may include the compound represented by Chemical Formula 3 or the pharmaceutically acceptable salt thereof (B), as an effective component. Herein, (B) may be one or a mixture two or more.

The cosmetic composition for whitening according to an embodiment of the present invention may be a mixture including the compound represented by Chemical Formula 2 or the pharmaceutically acceptable salt thereof (A) and the compound represented by Chemical Formula 3 or the pharmaceutically acceptable salt thereof (B) as an effective component.

The cosmetic composition for whitening according to an embodiment of the present invention may include 0.0001 to 10 wt % of the effective component, based on the total weight of the composition, in terms of implementing a substantial autophagy activation effect. Considering the effect relative to the content, the effective component may be included specifically at 0.0005 to 5 wt %, more specifically 0.001 to 1 wt %, and most specifically 0.001 to 0.1 wt %.

Moreover, the cosmetic composition for whitening according to an embodiment of the present invention may include a mixture of a melanosome degradation inducing compound by autophagy activation and a melanosome transfer inhibition inducing compound by endocytosis inhibition simultaneously, as an effective component, for implementing a more improved whitening effect As an example, the melanosome degradation inducing compound by autophagy activation may be at least one compound selected from the compound represented by Chemical Formula 2 (A) and the melanosome transfer inhibition inducing compound by endocytosis inhibition may be at least one compound selected from the compound represented by Chemical Formula 3 (B).

Of course, in the cosmetic composition for whitening according to an embodiment of the present invention, a mixture of the melanosome degradation inducing compound by autophagy activation and the melanosome transfer inhibition inducing compound by endocytosis inhibition may be used at an appropriate weight ratio, depending on the application form, use purpose, and desired effect.

As an example, the mixture may be mixed at a weight ratio (A:B) of 1:0.1 to 1:1.

As an example, the mixture may be mixed at a weight ratio (A:B) of 1:0.1 to 1:0.8.

As an example, the mixture may be mixed at a weight ratio (A:B) of 1:0.1 to 1:0.5.

The cosmetic composition for whitening may be formulated into a common emulsion formulation, a solubilization formulation, and the like, using a commonly known preparation method.

As an example, the cosmetic composition for whitening may be formulated into a formulation selected from the group consisting of a softening lotion, an astringent, a nutritional lotion, an eye cream, a nutritional cream, a massage cream, powder, essence, and a pack.

As an example, the cosmetic composition for whitening may be formulated into a formulation selected from the group consisting of soap, a cleansing cream, a cleansing foam, cleansing water, and the like.

In addition, the cosmetic composition for whitening may further include an additional additive appropriately depending on the purpose. As an example, the additive may be one or more aqueous additives selected from the group consisting of a stabilizer, an emulsifier, a thickening agent, a moisturizer, a liquid crystal film enhancer, a pH controlling agent, an antimicrobial, an aqueous polymer, a coating agent, a metal ion sequestering agent, an amino acid, an organic amine, a polymer emulsion, a pH adjusting agent, a skin nutrient, an anti-oxidant, an anti-oxidant auxiliary agent, a preservative, flavoring, and the like; one or more oil-based additives selected from the group consisting of fat and oils, waxes, a hydrocarbon oil, a higher fatty acid oil, higher alcohol, a synthetic ester oil, silicone oil, and the like; and the like.

Herein, each of the additives may be included at 0.001 to 20 wt %, specifically at 0.01 to 10 wt %, or at 0.05 to 10 wt %, based on the total weight of the composition, but is not limited thereto.

The use according to an embodiment of the present invention may be a pharmaceutical composition for improving or treating a melanin hyperpigmentation disorder.

In addition, the use according to an embodiment of the present invention may be a method of alleviating or treating a melanin hyperpigmentation disorder. Specifically, the method may be applying an effective amount of the compound represented by Chemical Formula 1 or the pharmaceutically acceptable salt thereof to a skin of a subject in need thereof, and the skin of the subject in need thereof may be a skin with a melanin hyperpigmentation disorder.

Herein, the effective amount is not limited as long as it is within a range of usage of the above-descried effective component.

The pharmaceutical composition for improving or treating a melanin hyperpigmentation disorder according to an embodiment of the present invention may include the compound represented by Chemical Formula 1 or the pharmaceutically acceptable salt thereof as an effective component.

The compound represented by Chemical Formula 1 or the pharmaceutically acceptable salt thereof exhibits an excellent effect on improvement, prevention, and treatment of a melanin hyperpigmentation disorder, by implementing an excellent whitening effect. Specifically, the compound represented by Chemical Formula 1 according to embodiments of the present invention or the pharmaceutically acceptable salt thereof may increase the expression of autophagy-related protein to activate autophagy, thereby protecting cells from oxidation stress, and may improve, prevent, and treat various diseases and phenomena caused by oxidation stress. In particular, the compound represented by Chemical Formula 1 according to embodiments of the present invention or the pharmaceutically acceptable salt thereof induces melanosome degradation to decrease melanin production and to inhibit maturation of melanosomes and effectively inhibits endocytosis of keratinocytes to inhibit transfer of melanosomes, thereby being very effective in improvement, prevention, and treatment of a hyperpigmentation disorder induced from melanin.

The hyperpigmentation disorder may be freckles; senile plaque; liver spots; chloasma; brown or black spots; sunlight pigmented spots; cyanic melasma; hyperpigmentation after using drugs; chloasma gravidarum; hyperpigmentation after inflammation; and the like, but is not limited thereto.

The pharmaceutical composition for improving or treating a melanin hyperpigmentation disorder according to an embodiment of the present invention may include the compound represented by Chemical Formula 2 or the pharmaceutically acceptable salt thereof (A') as an effective component. Herein, (A') may be one or a mixture of two or more.

The pharmaceutical composition for improving or treating a melanin hyperpigmentation disorder according to an embodiment of the present invention may include the compound represented by Chemical Formula 3 or the pharmaceutically acceptable salt thereof (B') as an effective component. Herein, (B') may be one or a mixture two or more.

The pharmaceutical composition for improving or treating a melanin hyperpigmentation disorder according to an embodiment of the present invention may be a mixture including the compound represented by Chemical Formula 2 or the pharmaceutically acceptable salt thereof (A') and the compound represented by Chemical Formula 3 or the pharmaceutically acceptable salt thereof (B') as an effective component.

The pharmaceutical composition for improving or treating a melanin hyperpigmentation disorder according to an embodiment of the present invention may include 0.0001 to 10 wt % of the effective component, based on the total weight of the composition, in terms of implementing a substantial autophagy activation effect. Considering the effect relative to the content, the effective component may be included specifically at 0.001 to 5 wt %, more specifically 0.001 to 1 wt %, and most specifically 0.001 to 0.1 wt %.

Moreover, the pharmaceutical composition for improving or treating a melanin hyperpigmentation disorder according to an embodiment of the present invention may include a mixture of a melanosome degradation inducing compound by autophagy activation and a melanosome transfer inhibition inducing compound by endocytosis inhibition, as an effective component, for implementing a more improved effect.

As an example, the melanosome degradation inducing compound by autophagy activation may be at least one compound selected from the compound represented by Chemical Formula 2 (A') and the melanosome transfer inhibition inducing compound by endocytosis inhibition may be at least one compound selected from the compound represented by Chemical Formula 3 (B').

Of course, in the pharmaceutical composition for improving or treating a melanin hyperpigmentation disorder according to an embodiment of the present invention, a mixture of the melanosome degradation inducing compound by autophagy activation and the melanosome transfer inhibition inducing compound by endocytosis inhibition may be used at an appropriate weight ratio, depending on the application form, use purpose, and desired effect.

As an example, the mixture may be mixed at a weight ratio (A':B') of 1:0.1 to 1:1.

As an example, the mixture may be mixed at a weight ratio (A':B') of 1:0.1 to 1:0.8.

As an example, the mixture may be mixed at a weight ratio (A':B') of 1:0.1 to 1:0.5.

The pharmaceutical composition for improving or treating a melanin hyperpigmentation disorder may be formulated into a formulation including a pharmaceutically acceptable carrier, using a commonly known preparation method.

As an example, the pharmaceutical composition for improving or treating a melanin hyperpigmentation disorder may be formulated into a formulation for external skin selected from the group consisting of a lotion, an ointment, gel, cream, a patch, a spraying agent, and the like.

As an example, the pharmaceutical composition for improving or treating a melanin hyperpigmentation disorder may be formulated into formulations for oral (tablets, capsules, or powders), intraoral, sublingual, intrarectal, vaginal, intranasal, topical, or parenteral (including intravenous, intracavernous, intramuscular, subcutaneous, and intraluminal) administration.

In addition, the pharmaceutical composition for improving or treating a melanin hyperpigmentation disorder may include a further pharmaceutically acceptable carrier appropriately depending on the purpose. As an example, the additive may be lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, or mineral oil, but is not limited thereto. In addition, a carrier such as a lubricant, a wetting agent, a sweetener, a flavoring agent, an emulsifier, a suspending agent, or a preservative may be further included.

Herein, each of the carriers may be included at 0.001 to 20 wt %, specifically at 0.01 to 10 wt %, or at 0.05 to 10 wt %, based on the total weight of the composition, but is not limited thereto.

Hereinafter, the present invention will be described in detail by Examples. However, the following Examples are only illustrative of the present invention, and do not limit the present invention in any way.

(Example 1) Synthesis of Compound 1

Step 1. Synthesis of Compound 1a
(Fmoc-Lys(Dde)-O-2-chloro Trityl Resin)

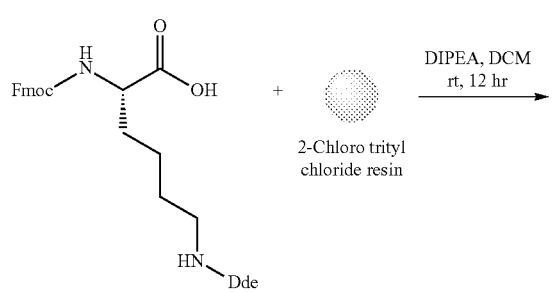

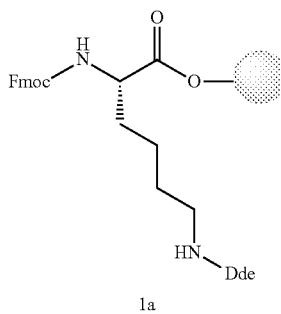

1a

A 2-chloro trityl chloride resin (100-200 mesh, Novabiochem 100 mg, 1 eq.), Fmoc-Lys(Dde)-OH (Nα-Fmoc-Nε-Dde-L-lysine, Nα-Fmoc-Nε-[1-(4,4-dimethyl-2,6-dioxocyclohexylidene)ethyl]-L-lysine) (106.5 mg, 2 eq.), and diisopropylamine (DIPEA, 69.7 μl, 4 eq.) dissolved in 5 ml of dichloromethane (DCM) were added to a 10 ml reaction vessel, and were reacted at room temperature (23° C.) for 12 hours. The reaction solution was removed by filtration, and the synthesized resin was subsequently washed using 10 ml of each of dichloromethane and methanol (MeOH), dichloromethane, and dimethylformamide (DMF), thereby quantitatively obtaining Compound 1a.

Step 2. Synthesis of Compound 1b (Fmoc-Lys(Fmoc)-Lys(Dde)-O-2-chloro Trityl Resin)

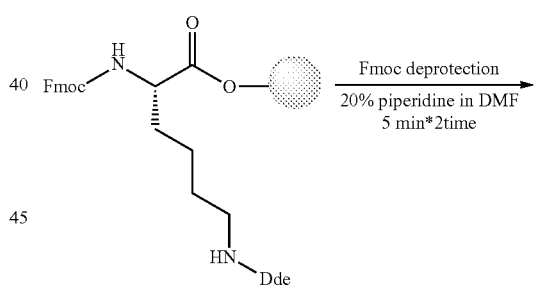

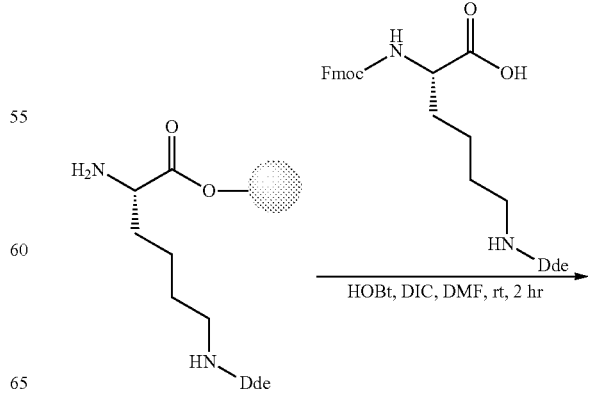

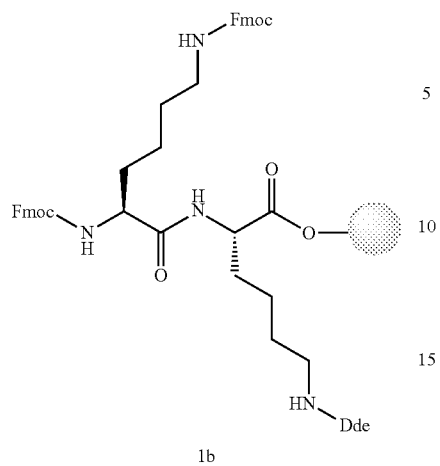

1b 5 ml of 20% piperidine (in DMF) was added to the reaction vessel of step 1 (Compound 1a obtained in step 1), reacted at room temperature for 5 minutes, and filtered to remove the reaction solution. 5 ml of 20% piperidine (in DMF) was added once more, and reacted at room temperature for 5 minutes. The reaction solution was removed by filtration, the synthesized resin was sequentially washed with 10 ml of each of DCM and MeOH, DCM, and DMF, Fmoc-Lys(Fmoc)-OH (236.3 mg, 4 eq.), hydroxybenzotriazole (HOBt, 54.1 mg, 4 eq.), and N,N-diisopropylcarbodiimide (DIC, 61.9 μl, 4 eq.) dissolved in 5 ml of DMF were added, and reacted at room temperature for 2 hours. The reaction solution was removed by filtration, and the synthesized resin was subsequently washed using 10 ml of each of DCM and MeOH, DCM, and DMF, thereby quantitatively obtaining Compound 1b.

Step 3. Synthesis of Compound 1c (tert-butoxycarbonylmethyl)2-Lys(tert-butoxycarbonylmethyl)2-Lys (Dde)-O-2-chloro Trityl Resin)

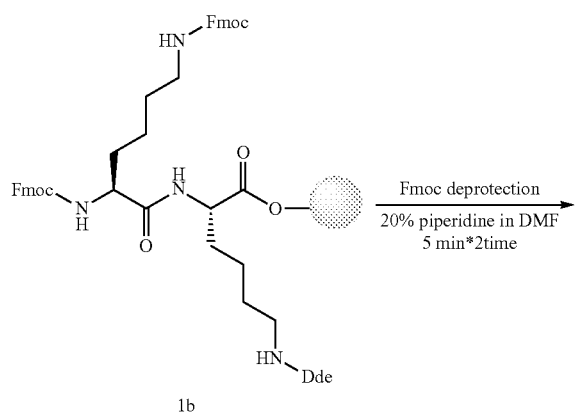

1b

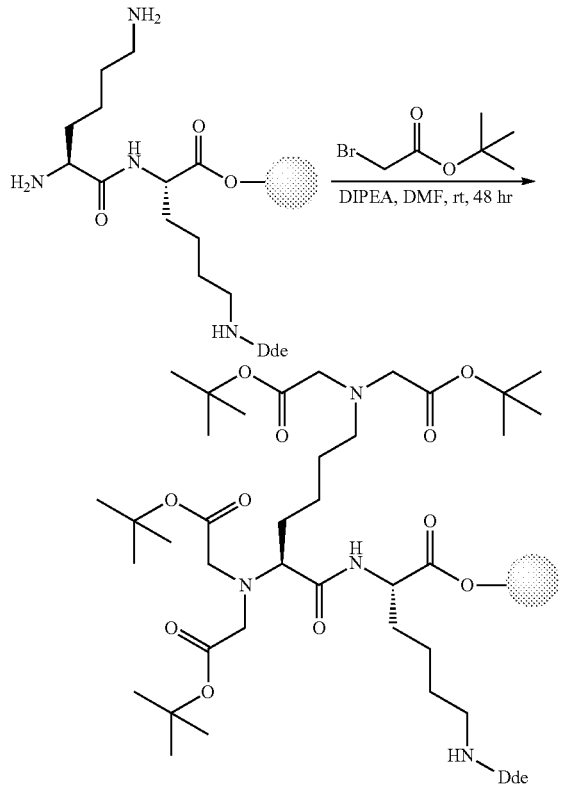

1c 5 ml of 20% piperidine (in DMF) was added to the reaction vessel of step 2 (Compound 1b obtained in step 2), reacted at room temperature for 5 minutes, and filtered to remove the reaction solution. 5 ml of 20% piperidine (in DMF) was added once more, and reacted at room temperature for 5 minutes. The reaction solution was removed by filtration, the synthesized resin was sequentially washed using 500 ml of each of DCM and MeOH, DCM, and DMF, t-butyl bromoacetate (147.7 μl, 10 eq.) and DIPEA (261.3 μl, 15 eq.) dissolved in 5 ml of DMF were added, and reacted at room temperature for 48 hours. The reaction solution was removed by filtration, and the synthesized resin was subsequently washed using 10 ml of each of DCM and MeOH, DCM, and DMF, thereby quantitatively obtaining Compound 1c.

Step 4. Synthesis of Compound 1d (tert-butoxycarbonylmethyl)2-Lys(tert-butoxycarbonylmethyl)2-Lys (NH2)-O-2-chloro Trityl Resin)

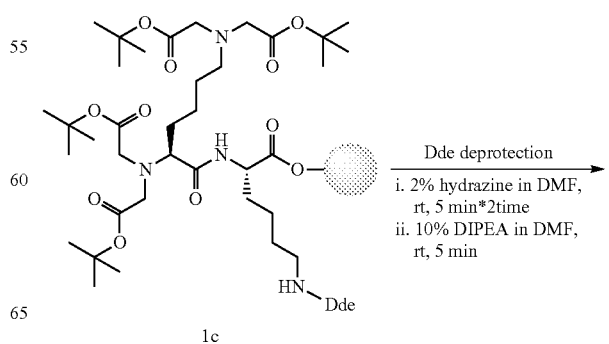

1c

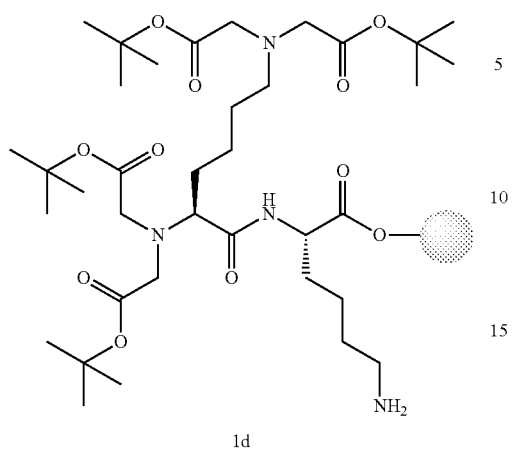

1d 5 ml of 2% hydrazine (in DMF) was added to the reaction vessel of step 3 (Compound 1c obtained in step 3) and reacted at room temperature for 5 minutes. The reaction solution was removed by filtration, the synthesized resin was washed using 10 ml of DMF, 10 ml of 10% DIPEA (in DMF) was added, and reacted at room temperature for 5 minutes. The reaction solution was removed by filtration, and the synthesized resin was subsequently washed using 10 ml of each of DCM and MeOH, DCM, and DMF, thereby quantitatively obtaining Compound 1d.

Step 5. Synthesis of Compound 1

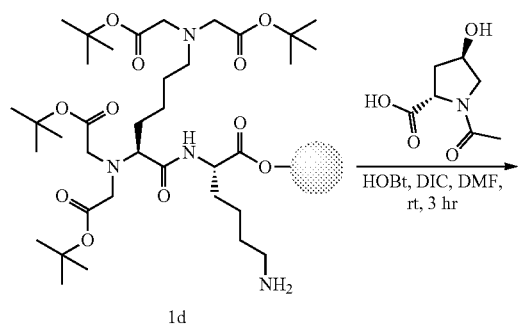

1d

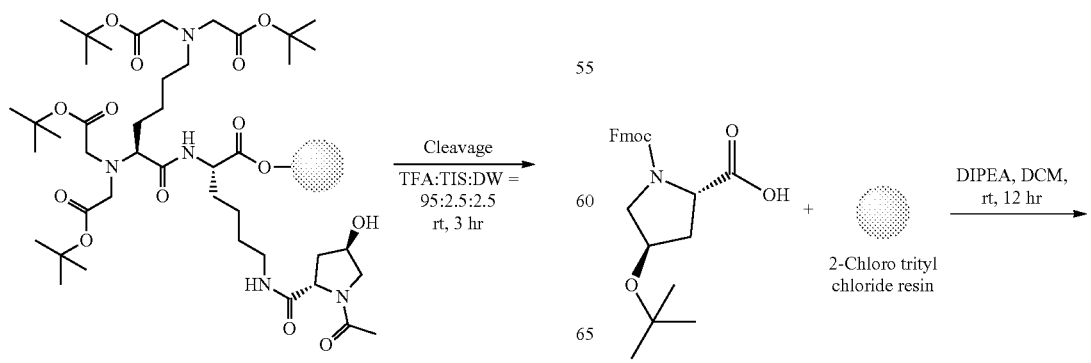

1

N-Acetyl-L-hydroxyproline (138.5 mg, 8 eq.), HOBt (180.1 mg, 8 eq.), and DIC (123.9 µl, 8 eq.) dissolved in 5 ml of DMF were added to the reaction vessel of step 4 (Compound 1d obtained in step 4), and reacted at room temperature for 3 hours. The reaction solution was removed by filtration, and the synthesized resin was sequentially washed using 10 ml of each of DCM and DMF, and DCM.

After vacuum drying, 5 ml of a cleavage cocktail (trifluoro acetic acid:triisopropylsilane:DW=95:2.5:2.5) was added thereto, and reacted at room temperature for 3 hours. Filtering was carried out to collect the reaction solution, and ml of diethyl ether was added thereto to precipitate the product. A centrifuge was used to collect a solid product, which was washed twice with 45 ml of diethyl ether. The obtained solid product was purified using Prep-HPLC (column C18, 10 µm, 250 mm×22 mm), and then lyophilized to obtain 36.4 mg of Compound 1 (molecular weight measured by LC mass: 661.66) in a total yield of 55%.

(Example 2) Synthesis of Compound 2

Step 1. Synthesis of Compound 2a
(Fmoc-Hyp(tBu)-O-2-chloro Trityl Resin)

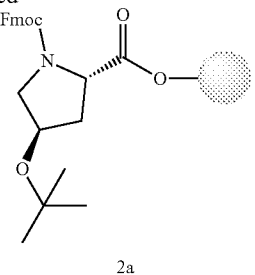

A 2-chlorotrityl chloride resin (100-200 mesh, Novabiochem 200 mg, 1 eq.), Fmoc-Hyp(tBu)-OH (Fmoc-O-tert-butyl-L-hydroxyproline) (163.8 mg, 2 eq.), and DIPEA (139.3 μl, 4 eq.) dissolved in 5 ml of DCM were added to a 10 ml of reaction vessel, and reacted at room temperature for 12 hours. The reaction solution was removed by filtration, and the synthesized resin was subsequently washed using 10 ml of each of DCM and MeOH, DCM, and DMF, thereby quantitatively obtaining Compound 2a.

Step 2. Synthesis of Compound 2b (Fmoc-Lys (Fmoc)-Hyp(tBu)-O-2-chloro Trityl Resin)

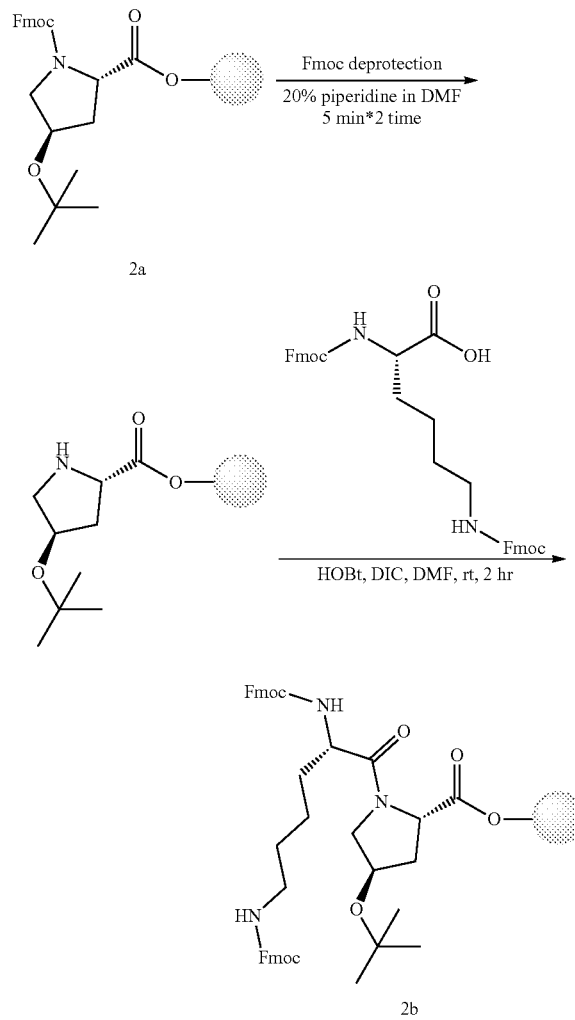

5 ml of 20% piperidine (in DMF) was added to the reaction vessel of step 1 (Compound 2a obtained in step 1), reacted at room temperature for 5 minutes, and filtered to remove the reaction solution. 5 ml of 20% piperidine (in DMF) was added once more, and reacted at room temperature for 5 minutes. The reaction solution was removed by filtration, the synthesized resin was sequentially washed with 10 ml of each of DCM and MeOH, DCM, and DMF, Fmoc-Lys(Fmoc)-OH (472.6 mg, 4 eq.), HOBt (108.1 mg, 4 eq.), and DIC (123.9 μl, 4 eq.) dissolved in 5 ml of DMF were added, and reacted at room temperature for 2 hours. The reaction solution was removed by filtration, and the synthesized resin was subsequently washed using 10 ml of each of DCM and MeOH, DCM, and DMF, thereby quantitatively obtaining Compound 2b.

Step 3. Synthesis of Compound 2c (tert-butoxycarbonylmethyl)2-Lys(tert-butoxycarbonylmethyl)2-Hyp(tBu)-O-2-chloro Trityl Resin)

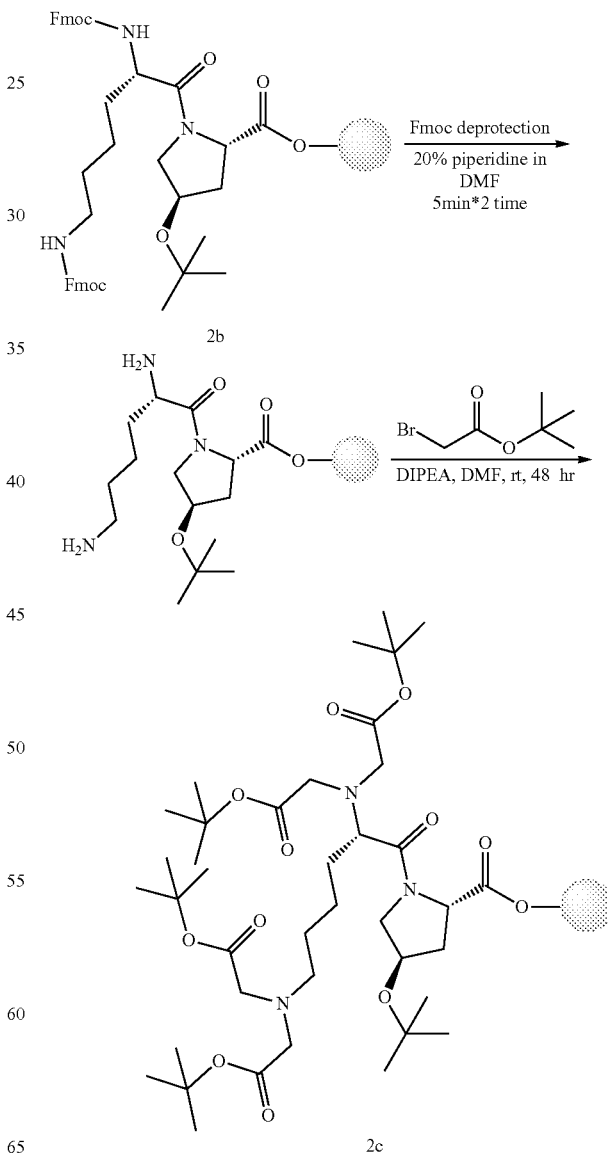

5 ml of 20% piperidine (in DMF) was added to the reaction vessel of step 2 (Compound 2b obtained in step 2), reacted at room temperature for 5 minutes, and filtered to remove the reaction solution. 5 ml of 20% piperidine (in DMF) was added once more, and reacted at room temperature for 5 minutes. The reaction solution was removed by filtration, the synthesized resin was sequentially washed using 500 ml of each of DCM and MeOH, DCM, and DMF, t-butyl bromoacetate (295.3 μl, 10 eq.) and DIPEA (522b μl, 15 eq.) dissolved in 5 ml of DMF were added, and reacted at room temperature for 48 hours. The reaction solution was removed by filtration, and the synthesized resin was subsequently washed using 10 ml of each of DCM and DMF, and DCM, thereby quantitatively obtaining Compound 2c.

Step 4. Synthesis of Compound 2

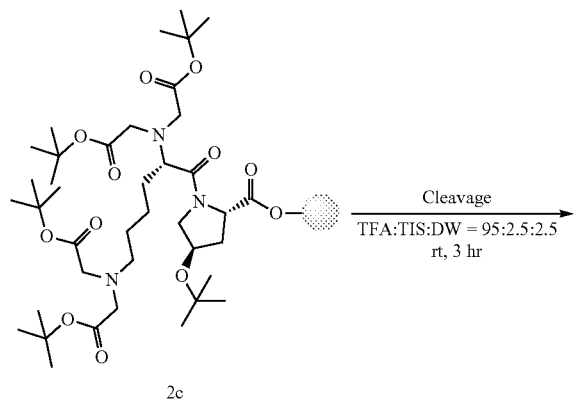

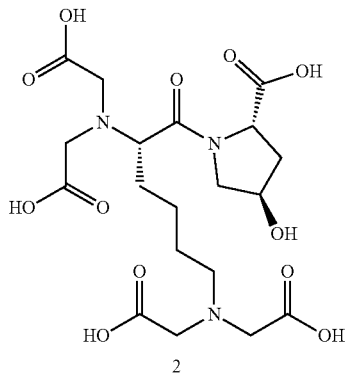

5 ml of a cleavage cocktail (trifluoro acetic acid:triisopropylsilane:DW=95:2.5:2.5) was added to the reaction vessel of step 3 (Compound 2c obtained in step 3) and reacted at room temperature for 3 hours. The reaction solution was collected by filtration, and diethyl ether was added to precipitate the product. A centrifuge was used to collect a solid product, which was washed twice with 45 ml of diethyl ether. The obtained solid product was purified using Prep-HPLC (column C18, 10 μm, 250 mm×22 mm), and then lyophilized to obtain 59 mg of Compound 2 (molecular weight measured by LC mass: 491.45) in a total yield of 60%.

(Example 3) Confirmation of Tyrosinase Inhibition

In order to analyze whether Compound 1 and Compound 2 obtained in the above Examples inhibit tyrosinase activity, a tyrosinase activity inhibition assay was performed.

As a specific experimental method, mushroom tyrosinase was diluted with a 0.1 M sodium phosphate buffer at 2 unit/ul and dissolved in water at 0.03 wt % of tyrosine. Each experiment group listed in the following Table 1 was also diluted in the 0.1 M sodium phosphate buffer at 10, 100, 1000, and 10000 ppm and mixed as listed in Table 1. Reaction was performed at 37° C. for 1 hour and absorbance was measured, respectively (wavelength: 490 nm, Epoch, BioTek). Based on the results, a tyrosinase inhibition ratio relative to a control group was calculated.

Figure 2:
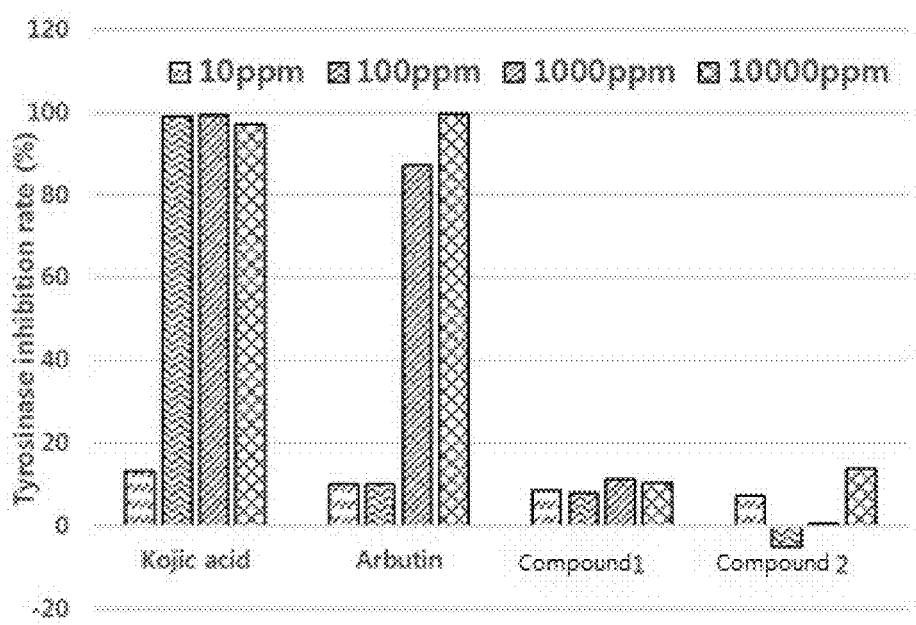
FIG. 2 shows a result of confirming whether the compound according to an embodiment of the present invention inhibits tyrosinase activity.

The results are shown in FIG. 2.

As seen from FIG. 2, it was confirmed that Compound 1 and Compound 2 did not inhibit tyrosinase activity at all concentrations.

TABLE 1

|  | Control group | Experimental group 1 | Experimental group 2 | Experimental group 3 | Experimental group 4 |
|---|---|---|---|---|---|
| 0.1 M Sodium phosphate | 240 ul | 210 ul | 210 ul | 210 ul | 210 ul |
| Tyrosine 0.03% | 40 ul | 40 ul | 40 ul | 40 ul | 40 ul |
| Mushroom tyrosinase | 20 ul | 20 ul | 20 ul | 20 ul | 20 ul |
| Sample | — | 30 ul (Compound 1) | 30 ul (Compound 2) | 30 ul (Arbutin) | 30 ul (Kojic acid) |
| Total | 300 ul | 300 ul | 300 ul | 300 ul | 300 ul |

Arbutin: Arbutin,
kojic acid: Kojic acid,
control group: Blank (Example 4) Confirmation of Appropriate Treatment Concentration In order to confirm a treatment concentration of Compound and Compound 2 obtained in the above Examples having no cytotoxicity thereby, an MTT assay was performed.

As a specific experimental method, in order to confirm cytotoxicity depending on the treatment concentration of Compound 1 and Compound 2, apoptosis analysis was performed in melanin cells (human primary melanocyte, HEMn-DP, cat # C2025C, Gibco) and keratinocytes (human primary keratinocyte, HEKn, cat # C0015C, Gibco). Cells were deposited to the number of 1×10$^4$ cells/well in a 96 well plate and cultured in an incubator for 24 hours under the condition of 37° C. and 5% $CO_2$.

Each of Compound 1 and Compound 2 obtained in the above Examples was dissolved in distilled water (DW) at a concentration of 100 mM to form a concentrated solution, which was diluted with a medium, and treatment was performed at concentrations of 5, 10, and 50 μM. After 4 days, the medium of the plate was removed and the plate was treated with 100 μl of an MTT reagent (Sigma, 0.5 mg/ml). After 4 hours, the reagent was removed, dimethyl sulfoxide (DMSO) was added thereto, and absorbance was measured (wavelength: 570 nm, Epoch, BioTek). Here, cell viability was calculated as a percentage to absorbance of a control group (blank) which was not treated with the compound. The results are shown in FIGS. 3 and 4.

Figure 3:
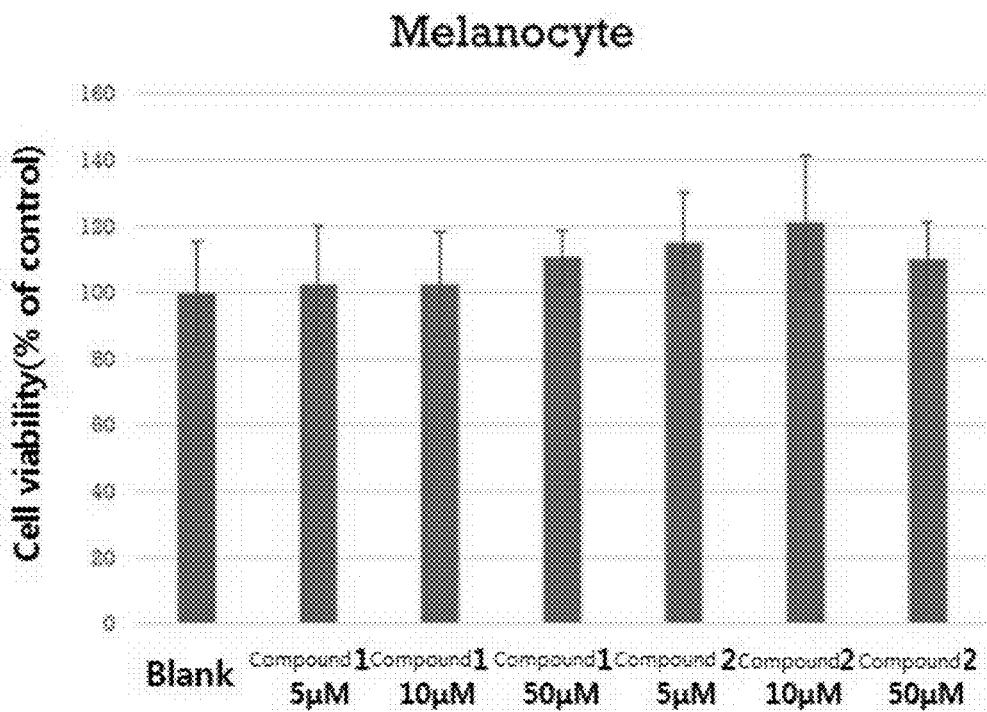
FIG. 3 is a drawing showing a result of performing an MTT assay in melanocytes, in order to confirm a treatment concentration of the compound according to an embodiment of the present invention without cytotoxicity.
Figure 4:
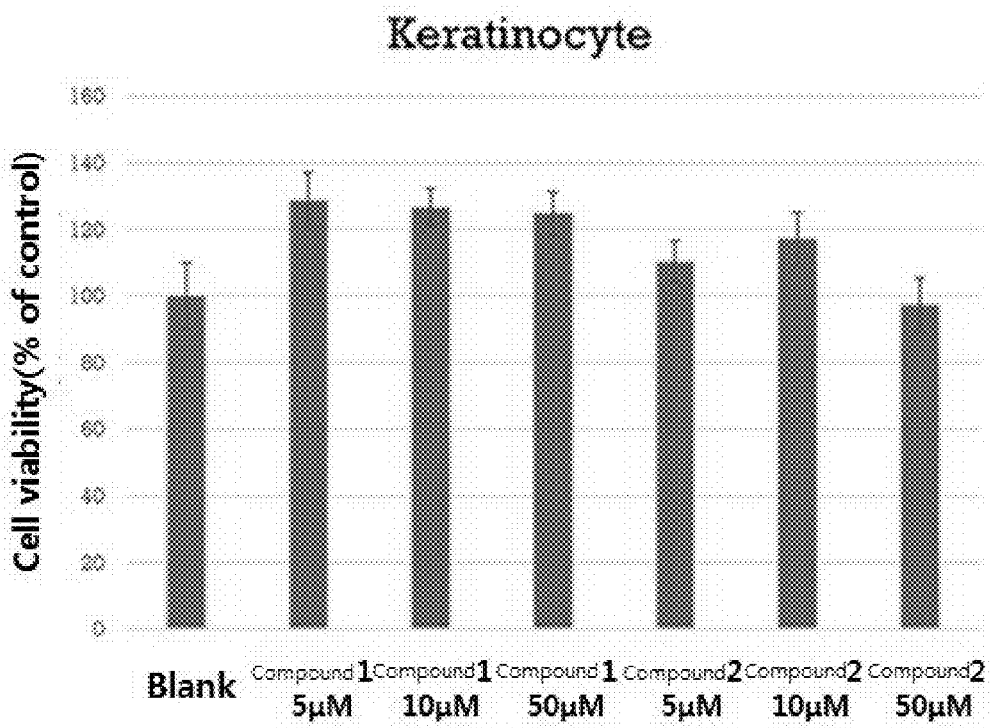
FIG. 4 is a drawing showing a result of performing an MTT assay in keratinocytes, in order to confirm a treatment concentration of the compound according to an embodiment of the present invention without cytotoxicity.

As seen from FIGS. 3 and 4, Compound 1 and Compound 2 were confirmed to have almost no cytotoxicity even at concentrations of 5, 10, and 50 μM. That is, the compound according to embodiments of the present invention was confirmed to have no cytotoxicity at the concentration in both melanin cells and keratinocytes. Thus, the subsequent experiments were performed at a concentration of 10 μM.

(Example 5) Confirmation of Change in Melanosome Maturation-Related Genes and Change in Melanin Content In order to analyze how Compound 1 and Compound 2 obtained in the above Examples affect melanosome maturation, an amount of melanosome maturation-related mRNA after treated with Compound 1 and Compound 2 was analyzed with qPCR and a melanin content was measured with absorbance.

As a specific experimental method, human-derived melanin cells (HEMn-DP, cat # C2025C, Gibco) were constantly deposited to the number of $1 \times 10^5$ in a 6 well plate for culturing and cultured in an incubator for 24 hours under the condition of 37° C. and 5% $CO_2$ in M254 (cat # M-254-500, Gibco). Each of Compound 1 and Compound 2 was dissolved in DW at a concentration of 100 mM to form a concentration solution, which was diluted in a medium at a concentration of 20 μM, 1 ml of each diluted solution was added to each well containing 1 ml of the medium first for treatment and cultured for 48 hours, and RNeasy mini kit (cat #74106, QIAGEN) was used to extract RNA from melanin cells. Extracted RNA was synthesized into cDNA using a cDNA synthesis kit (cat # FSQ-201, TOYOBO), an MITF(F: TAA CCT GTA CAA CAA CTC TCG ATC TCA; R: GTT GGC CTC AGT CCC AGT TC), Tyrosinase(F: AGC ACC CCA CAA ATC CTA ACT TAC; R: ATG GCT GTT GTA CTC CTC CAA TC) primer and POWER SYBR MASTER MIX (cat #4367659, Thermo) were mixed at a recommended ratio with the synthesized cDNA, and qPCR was performed with QuantStudio 3 equipment (cat # A28131, Thermo). Then, the experiment was performed identically, the medium was removed after completion of culturing, melanin cells were separated from the plate using Trypsin-EDTA (cat # LS-015-09, WELGENE), transferred to a 1.5 ml tube, and spun down, a photograph of the pellet was taken, and the absorbance of a solution of the pellet dissolved in 1N NaOH was measured (wavelength: 400 nm, Epoch, BioTek).

Figure 5:
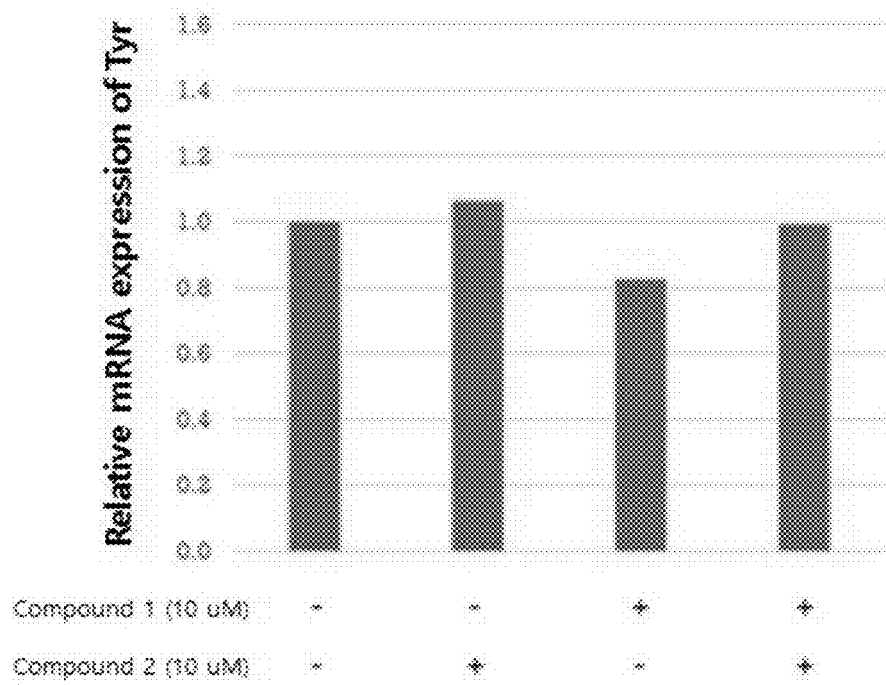
FIG. 5 shows a result of analyzing whether a change in expression of a gene (tyrosinase) related to maturation of melanosomes is affected by treatment with the compound according to an embodiment of the present invention.
Figure 6:
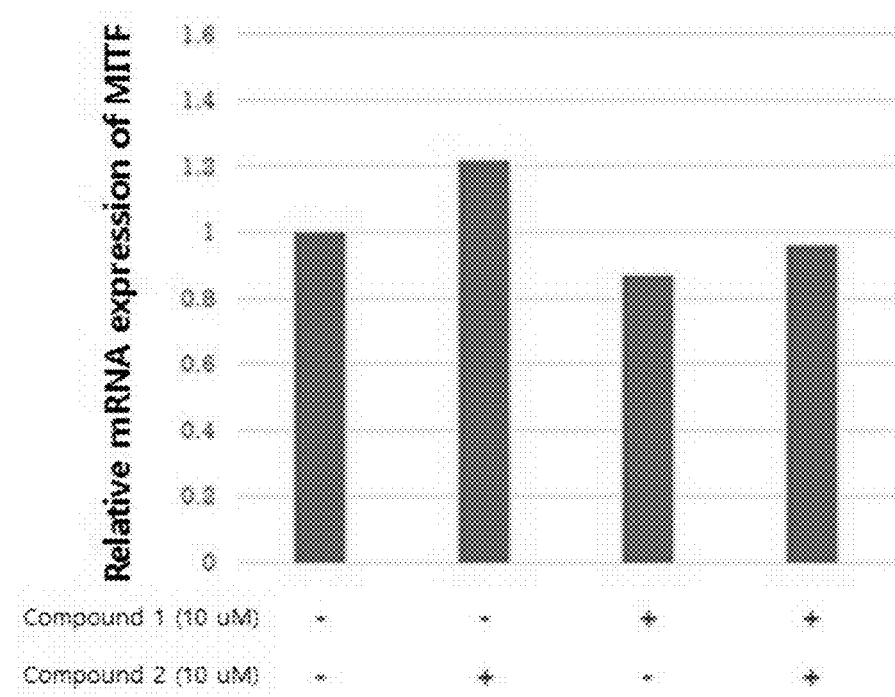
FIG. 6 shows a result of analyzing whether a change in expression of a gene (MITF) related to maturation of melanosomes is affected by treatment with the compound according to an embodiment of the present invention.
Figure 7:
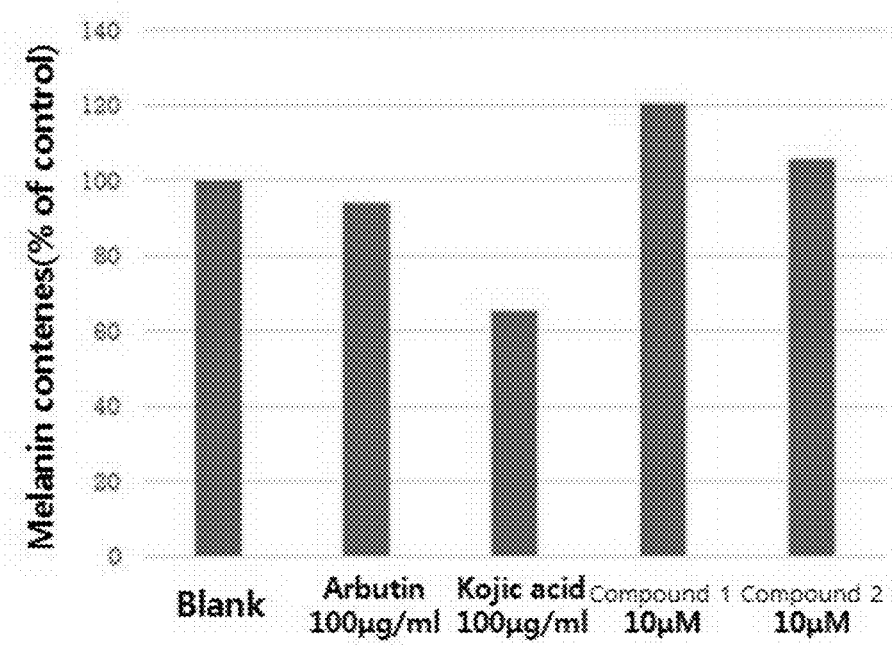
FIG. 7 shows a result of analyzing a changed melanin content by treatment with the compound according to an embodiment of the present invention.

The results are shown in FIGS. 5 to 7.

As seen from FIGS. 5 to 7, it was found that Compound 1 and Compound 2 obtained in the above Examples had almost no influence on melanosome maturation activity in melanin cells.

(Example 6) Confirmation of an Increase in Autophagy Activation Gene Expression s and Decrease in Endocytosis-Related Gene Expression in Keratinocytes For intracellular autophagy analysis by treatment with Compound 1 obtained in the above Example, a western blot was performed on a LC3 (light chain 3; autophagy marker) protein. In addition, for analysis of change in endocytosis-related genes by treatment with Compound 2 obtained in the above Example, qPCR was performed on PAR2, AAK1 (AP2 Associated Kinase 1).

As a specific experimental method, keratinocytes (HEKn, cat # C0015C, Gibco) was treated with Compound 1 and dissolved using a cell lysis buffer containing a proteolysis inhibitor. The entire dissolved solution was fractionized using a centrifuge and only the solution containing proteins was extracted. The extracted proteins were quantified by a bicinchoninic acid (BCA) method. 20 μg of proteins were separated by 10% SDS-polyacrylamide gel electrophoresis and transferred to a nitrocellulose film. The film to which the proteins were transferred was blocked by a tris-buffered saline/0.05% Tween-20 (TBS-T) solution containing 5% non-fat milk for decreasing a non-specific bonding at room temperature for 1 hour, and then a primary antibody was reacted under the condition of 4° C. overnight and a secondary antibody was reacted at room temperature for 1 hour. For visualization, an enhanced chemiluminescence system was used.

As a specific experimental method, from keratinocytes (HEKn, cat # C0015C, Gibco) treated with Compound 2, RNA was extracted using a RNeasy mini kit (cat #74106, QIAGEN), cDNA was synthesized using a cDNA synthesis kit (cat # FSQ-201, TOYOBO), and then a PAR2(F: CTC TCC TGC AGT GGC ACC AT; R: GAT GTG CCA TCA ACC TTA CCA A) primer and POWER SYBR MASTER MIX (cat #4367659, Thermo) were mixed at a recommended ratio with the synthesized cDNA, and qPCR was performed with QuantStudio 3 equipment (cat # A28131, Thermo).

Figure 8:
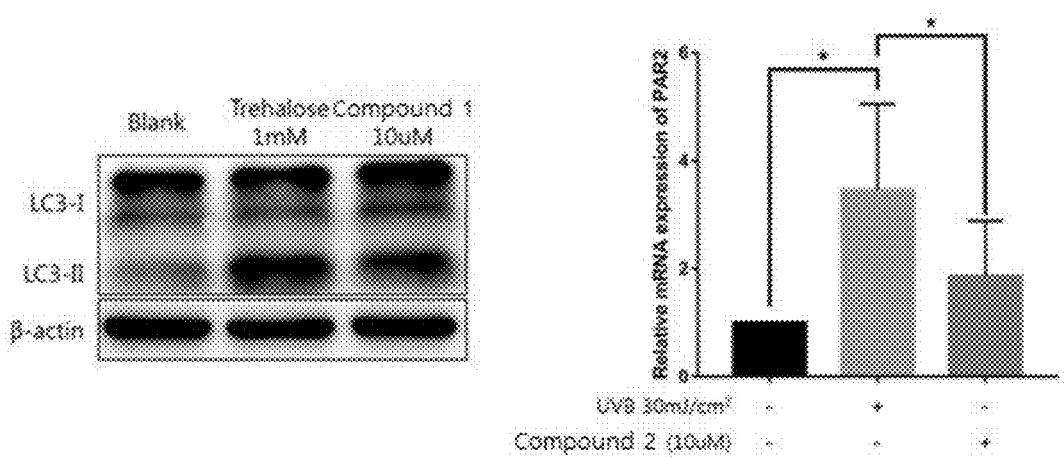
FIG. 8 shows a result of analyzing a change in expression of proteins related to autophagy activation and a change in mRNA of a gene related to endocytosis by treatment with the compound according to an embodiment of the present invention.

The results are shown in FIG. 8.

As seen from FIG. 8, it was confirmed that production of LC3-II (matured autophagosome) was increased by Compound 1 and it was found that expression of the PAR-2 gene was decreased by Compound 2.

(Example 7) Confirmation of Melanin Pigmentation Decrease

In order to analyze how Compound 1 and Compound 2 obtained in the above Examples affect melanin pigmentation, a degree of pigmentation inhibition by melanin treatment was analyzed.

As a specific experimental method, human-derived keratinocytes (HEKn, cat # C0015C, Gibco) were constantly deposited to the number of $1 \times 10^5$ in a 6 well plate for culturing and cultured in an incubator for 24 hours under the condition of ° C. and 5% $CO_2$ in EpiLife (cat # MEPI500CA, Gibco). Each of Compound 1 or Compound 2 obtained in the above Examples was dissolved at a concentration of 100 mM to form a concentration solution, which was diluted in a medium at a concentration of 20 μM, 1 ml of each diluted solution was added to each well containing 1 ml of the medium first for treatment and cultured for 48 hours, and 10 mg/ml of melanin was added by 2 μl at a time and culturing was further performed for 2 hours. The medium was removed after completion of culturing, cells were separated from the plate using Trypsin-EDTA (cat # LS-015-09, WELGENE), transferred to a 1.5 ml tube and spun down, a photograph of the pellet was taken, and the absorbance of a solution of the pellet dissolved in 1N NaOH was measured (wavelength: 400 nm, Epoch, BioTek).

Figure 9:
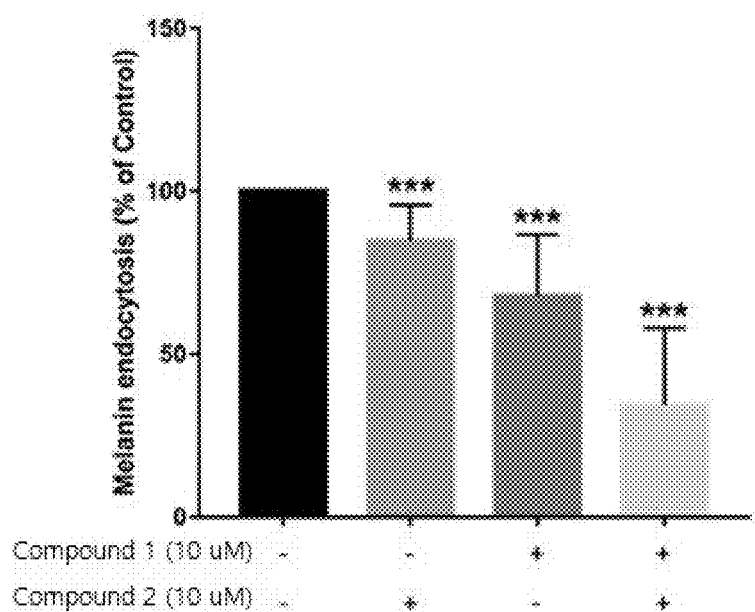
FIG. 9 shows a result of comparing and analyzing an effect of treatment with the compound according to an embodiment of the present invention on melanin pigmentation.

The results are shown in FIG. 9.

As seen from FIG. 9, it was confirmed that melanin pigmentation on keratinocytes was effectively inhibited by Compound 1 and Compound 2.

In addition, melanin pigmentation was better inhibited when treated with a mixture of Compound 1 and Compound 2 than when treated with Compound 1 or Compound 2 as a single compound.

(Example 8) Analysis of Whether Melanin Pigmentation Inhibition Activity Depends on Autophagy Activity In order to analyze whether melanin deposition inhibition activity on keratinocytes by treatment with Compound 1 and Compound 2 depends on autophagy activation, ATG5 which is the protein required for autophagy activation was knocked down and treated with melanin to analyze a pigmentation inhibition activity change.

As a specific experimental method, ATG5 siRNA was mixed according to the method of transfection reagent (RNAiMAX, cat #13778-075, Thermo) and deposited in keratinocytes (HEKn, cat # C0015C, Gibco). After 8 hours, Compound 1 and Compound 2 were diluted with Epilife (cat # MEPI500CA, Gibco) without a supplement and an antibiotic to a final concentration of 10 µM for treatment, and cells which were further cultured for 64 hours were dissolved using a cell lysis buffer containing a proteolysis inhibitor. The entire dissolved solution was fractionized using a centrifuge and only the solution containing proteins was extracted. The extracted proteins were quantified by a bicinchoninic acid (BCA) method. 20 µg of proteins were separated by 10% SDS-polyacrylamide gel electrophoresis and transferred to a nitrocellulose film. The film to which the proteins were transferred was blocked by a tris-buffered saline/0.05% Tween-20 (TBS-T) solution containing 5% BSA (bovine serum albumin, Gendepot, Cat # A0100-010) for decreasing a non-specific bonding at room temperature for 1 hour, and then a primary antibody was reacted under the condition of 4° C. overnight and a secondary antibody was reacted at room temperature for 1 hour. For visualization, an enhance chemiluminescence system was used. Then, in order to analyze melanin pigmentation inhibition activity, transfection and treatment with the compounds were performed identically, and then 10 mg/ml of melanin was added by 2 µl at a time and culturing was further performed for 2 hours. The culture medium was removed after completion of culturing, cells were separated from the plate using Trypsin-EDTA (cat # LS-015-09, WELGENE), transferred to a 1.5 ml tube and spun down, a photograph of the pellet was taken, and the absorbance of a solution of the pellet dissolved in 1N NaOH was measured (wavelength: 400 nm, Epoch, BioTek).

Figure 10:
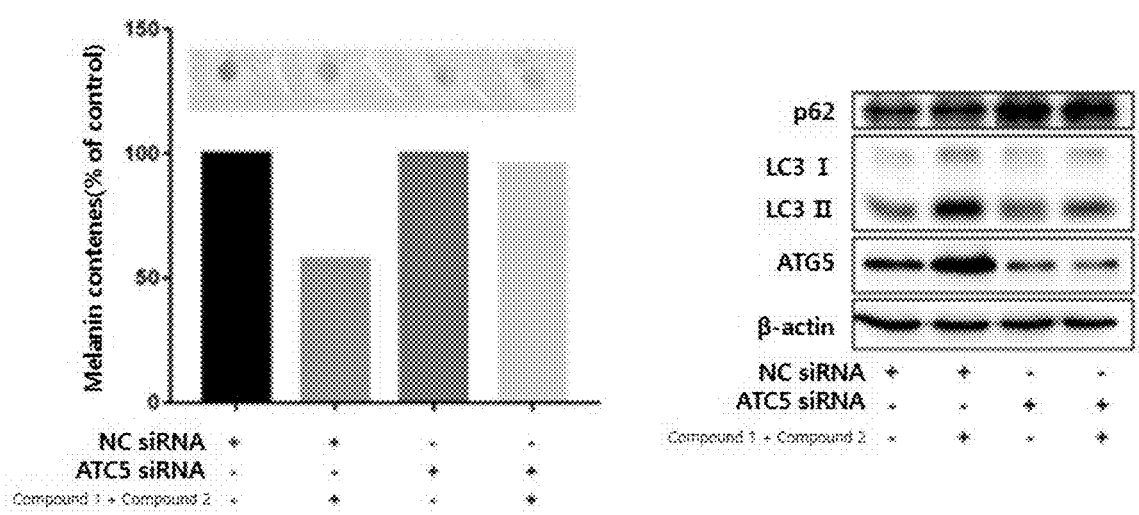
FIG. 10 confirms whether melanin pigmentation inhibition depends on autophagy by treatment with the compound according to an embodiment of the present invention, and shows a result of comparing and analyzing a changed melanin content in keratinocytes having knocked-down ATG5 and a change in proteins related to autophagy activation.

The results are shown in FIG. 10.

As seen from FIG. 10, it was confirmed that when ATG5 which is the protein required for autophagy activation was knocked down, a melanin amount in keratinocytes was not decreased by Compound 1 and Compound 2. In addition, it was confirmed that under the condition in which ATG5 was knocked down, expression activity of LC3-II and ATG5 which are autophagy proteins was inhibited by Compound 1 and Compound 2. Accordingly, it was found that melanin pigmentation inhibition activity by Compound 1 and Compound 2 depends on autophagy activity.

(Example 9) Melanosome Degradation Effect

In order to confirm whether melanosome and autuphagosome are co-localized by treatment with Compound 1 and Compound 2 obtained in the above Examples, analysis was performed with an electron microscope and a confocal microscope.

As a specific experimental method, Lysis Buffer (Tris 20 mM, NaCl 150 mM, EDTA 1 mM, sucrose 250 mM in DW) was added to melanin cells (HEMn-DP, cat # C2025C, Gibco) containing human-derived melanin at high concentration, freezing and thawing were repeated twice to break a cell membrane, and centrifugation was performed at 1000×g for 5 minutes, thereby obtaining a supernatant. Cushion Buffer (Tris 20 mM, NaCl 150 mM, EDTA 1 mM, sucrose 1.5M in DW) was placed in an ultracentrifuge tube, the same amount of supernatant was added thereto, and then centrifugation was performed under the conditions of 25,000 rpm, min, and 4° C., thereby obtaining melanosomes. The concentration of melanosomes was measured using synthesized melanin (cat # M8631, sigma) as a standard. Keratinocytes (HEKn, cat # C0015C, Gibco) was deposited in a 6 well by 1×10$^5$ cells/well at a time and cultured for one day. Treatment with 10 µM of Compound 1 and compound 2 each was performed, culturing was performed for one day, separated melanosomes (5 µg/well) was added, and culturing was further performed for 2 days. The culture medium was removed after completion of culturing, cells were fixed using a fixing solution for an electron microscope and fluorescein-labelled with an antibody (Pmel17, LC3), and it was confirmed with a confocal microscope whether melanosomes and autophagosomes were co-localized. In addition, cells which were experimented identically were observed as to the pattern of intracellular organelles with a transmission electron microscope.

Figure 11:
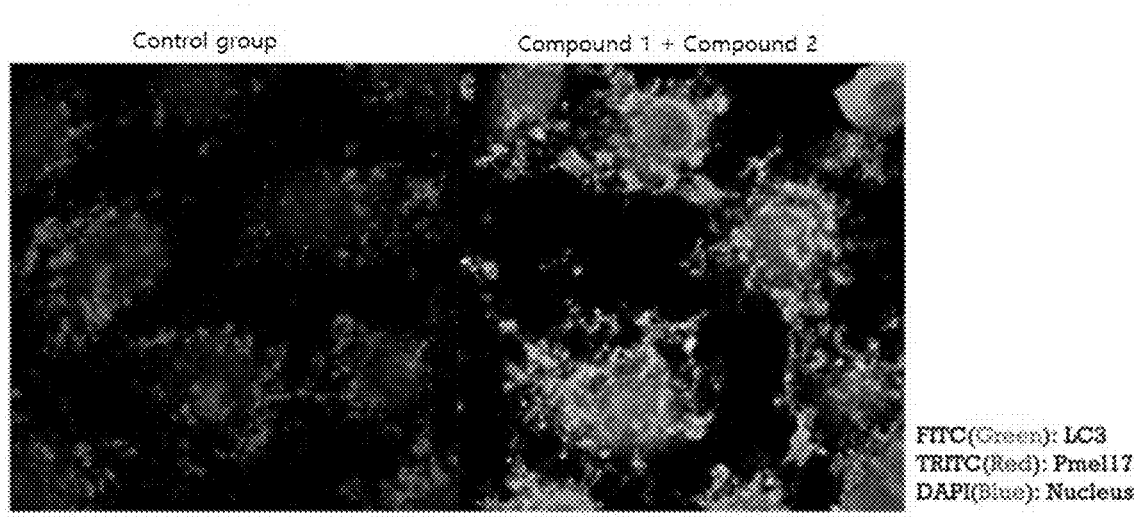
FIG. 11 shows a result of analyzing whether melanosomes are degraded by activated autophagy, through a confocal microscope, by treatment with the compound according to an embodiment of the present invention.
Figure 12:
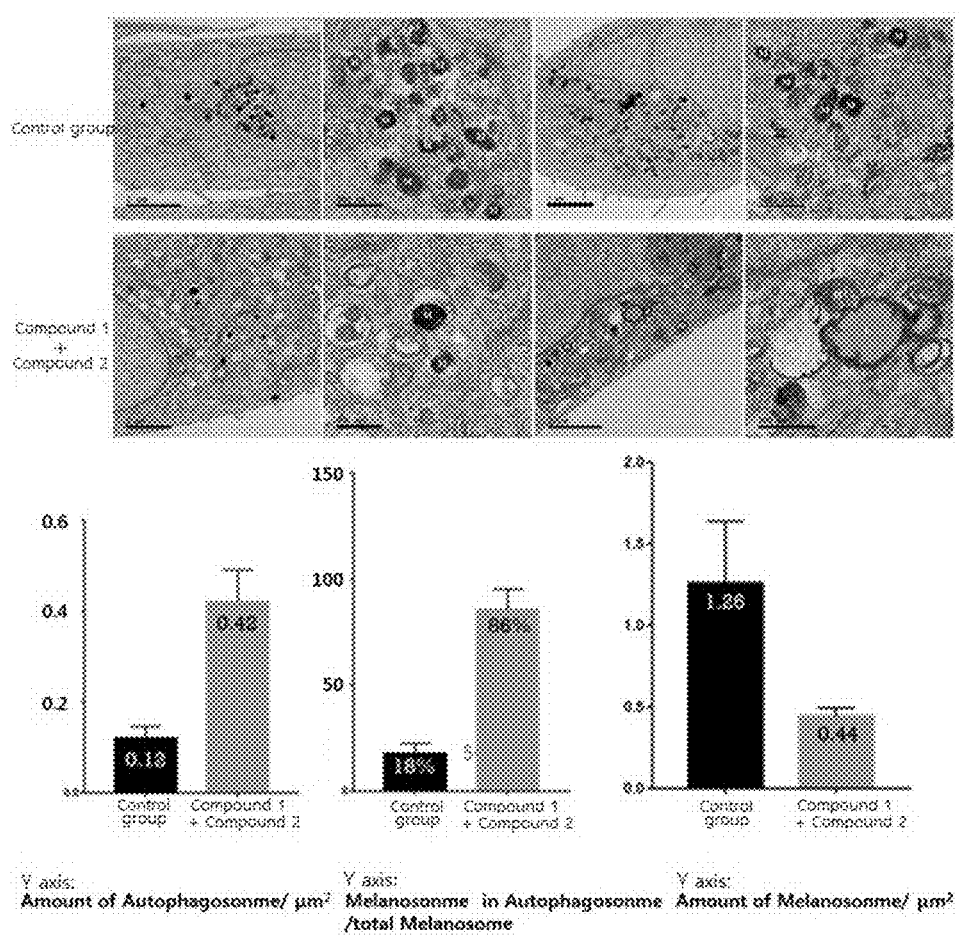
FIG. 12 shows a result of quantitatively analyzing whether melanosomes are degraded by activated autophagy, through an electron microscope (scale bar: 2 μm/500 nm/2 μm/500 nm), by treatment with the compound according to an embodiment of the present invention.

The results are shown in FIGS. 11 and 12.

As seen from FIG. 11, it was confirmed by a confocal microscope that autophagosomes increased by Compound 1 and Compound 2 were co-localized with melanosomes. In addition, it was confirmed that unlike control group in which more melanosomes are present in keratinocytes, when treated with a mixture of Compound 1 and Compound 2, melanosomes were rapidly degraded, so that the amount of melanosomes was significantly decreased.

In addition, as seen from FIG. 12, when treated with a mixture of Compound 1 and Compound 2, the phenomenon that 86% of the entire melanosomes are present in autophagosomes was confirmed by a transmission electron microscope.

(Example 10) Melanosome Deposition Inhibition Effect

In order to analyze whether melanosome deposition in keratinocytes is inhibited by treatment with Compound 1 and Compound 2, melanosomes separated from keratinocytes were treated and a melanin content and a melanosome indicator were analyzed.

As a specific experimental method, keratinocytes (HEKn, cat # C0015C, Gibco) were deposited in a 6 well by 1×10$^5$ cells/well at a time and cultured for one day, Compound 1 and Compound 2 were treated by 10 µM for one day, and melanosomes (5 µg/well) separated as in Example 9 were added thereto and further cultured for 2 days. The culture medium was obtained after completion of culturing, cells were separated from the plate using Trypsin-EDTA (cat # LS-015-09, WELGENE), transferred to a 1.5 ml tube, and spun down, a photograph of the pellet was taken, and the absorbance of a solution of the pellet dissolved in 1N NaOH was measured (wavelength: 400 nm, Epoch, BioTek).

In addition, for qualitative analysis thereof, a melanosome amount inside the culture medium and a cell pellet was analyzed using synthesized melanin (cat # M8631, sigma) as a standard. Like the pellet after lyophilization, the obtained culture medium was dissolved in 1N NaOH and the absorbance thereof was measured (wavelength: 400 nm, Epoch, BioTek).

Figure 13:
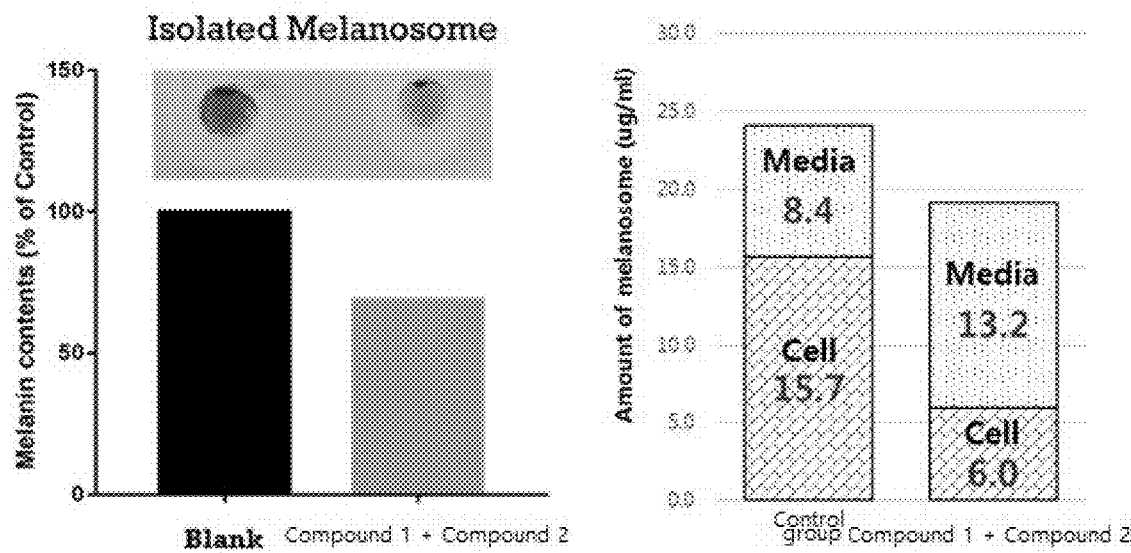
FIG. 13 shows a result of quantitatively analyzing melanosome pigmentation inhibition and degradation, by treatment with the compound according to an embodiment of the present invention.

The results are shown in FIG. 13.

As seen from FIG. 13, it was confirmed that when treated with a mixture of Compound 1 and Compound 2, the melanosome amount inside the keratinocytes is decreased, whereas the melanosome amount in the culture medium was increased. The result as such means that transfer of melanosomes into keratinocytes was effectively inhibited by treatment with a mixture of Compound 1 and Compound 2. Thus, when treatment with a mixture of Compound 1 and Compound 2 is performed, deposition of melanosomes may be significantly inhibited.

In addition, a mechanism in which a pigmentation process of keratinocytes according to embodiments of the present invention is inhibited is shown in the following FIG. 1.

(Example 11) Melanin Pigmentation Inhibition Effect

In order to analyze how Compound 1 and Compound 2 obtained in the above Examples histologically affect melanin pigmentation inhibition, a degree of melanin pigmentation inhibition was analyzed, using an artificial skin model.

As a specific experimental method, a black man-derived artificial skin model (MelanoDerm™, MEL-300-B, Mat-Tek) was cultured for 15 days under the conditions of 37° C., and 5% $CO_2$ in a dedicated medium (EPI-100-NMM-PRF). The surface of the artificial skin model was treated with 25 µl of Compound 1 and Compound 2 each obtained in the above Examples at a concentration of 100 ppm once every 24 hours. At the time of treatment with Compound 1 and Compound 2, treatment was performed after removing existing Compound 1 and Compound 2, and the medium was replaced every 24 hours. In the course of the experiment, the photographs of the tissue surface were taken on day 1, day 9, and day 15, and these results were used to analyze a degree of color change (L*value) on the tissue surface.

Figure 14:
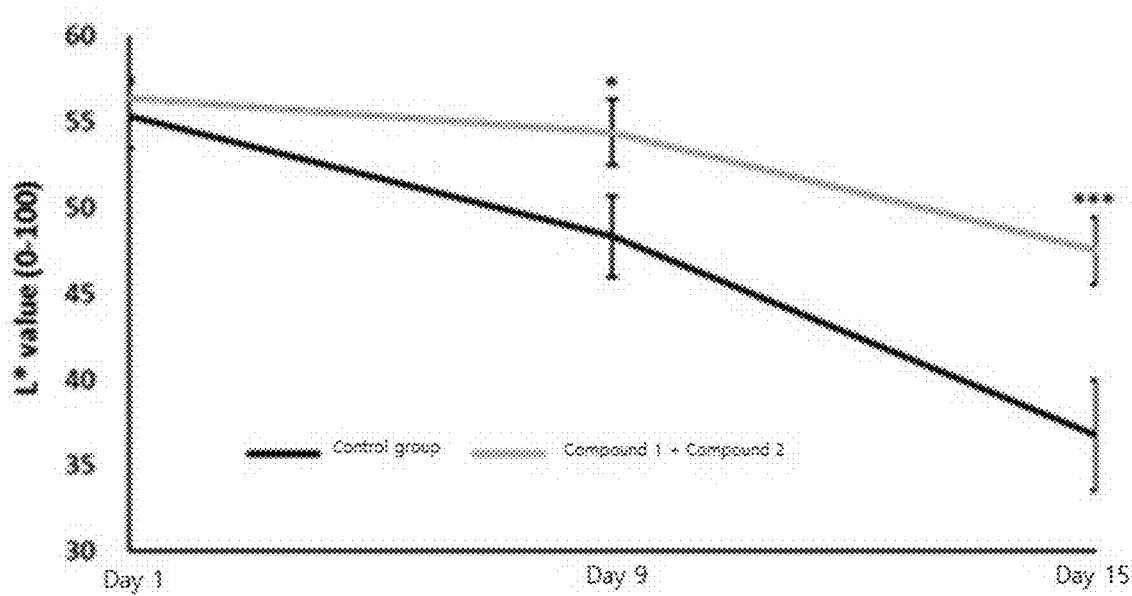
FIG. 14 is a result of confirming whether melanin pigmentation is decreased in an artificial skin model, by treatment with the compound according to an embodiment of the present invention.

The results are shown in FIG. 14.

As seen from FIG. 14, it was confirmed that melanin pigmentation was statistically significantly decreased in the group treated with a mixture of Compound 1 and Compound 2, as compared with the control group.

(Example 12) Melanin Degradation Effect

In order to analyze the melanin degradation effect of Compound 1 and Compound 2 obtained in the above Examples, an artificial skin model was used to analyze a melanin content.

As a specific experimental method, an artificial skin model was cultured as descried in Example 11. A tissue was obtained on day 15 and fixed in 4% phosphate buffered formalin for 24 hours. The fixed tissue was washed with running water for hours, dehydration was performed in an ascending order of alcohol concentration, and substitution with xylene and embedding with paraffin were performed. The paraffin embedded tissue was thinly cut at a thickness of 5 µm, and melanin was stained using a Fontana-Masson staining method and used for analysis. Photographs of the entire tissue and a stratum corneum part were analyzed with image J, respectively, and compared.

Figure 15:
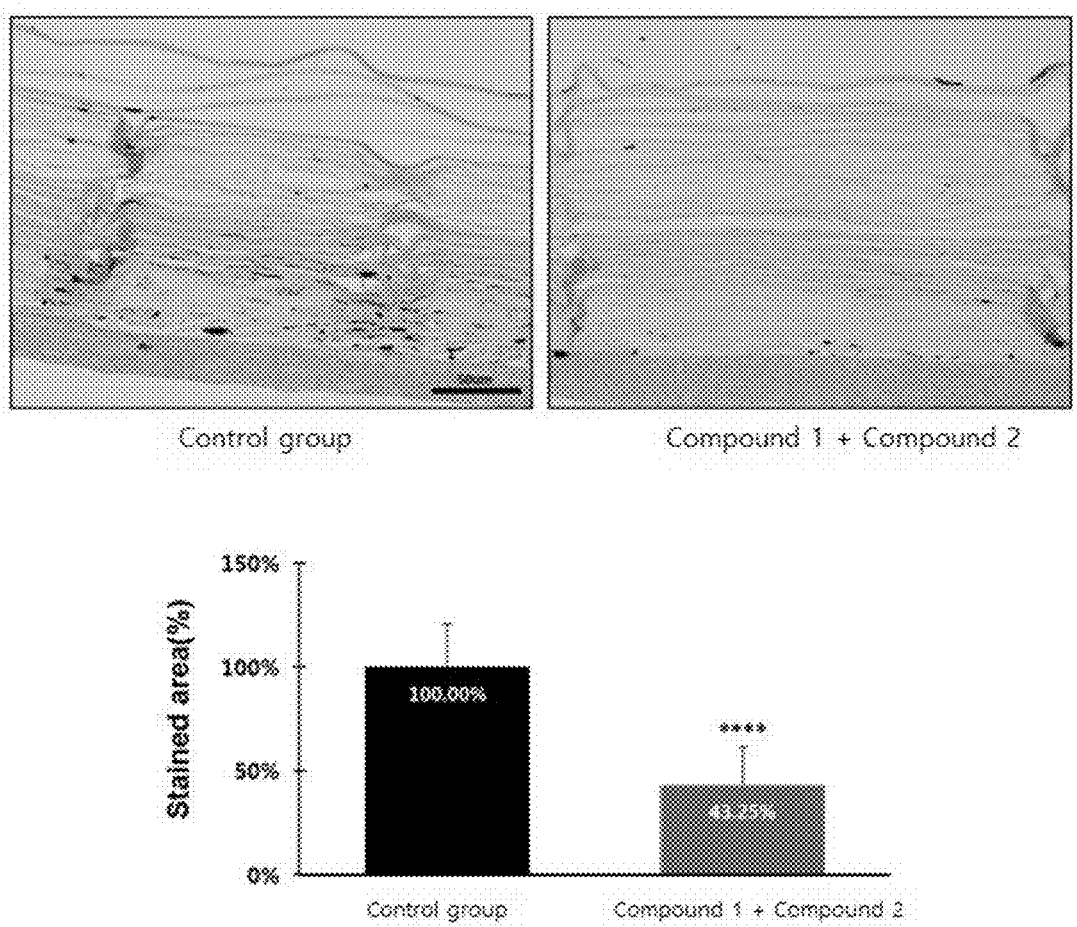
FIG. 15 shows a result of quantitatively analyzing a decrease in melanin pigmentation in an artificial skin model through F&M staining, by treatment with the compound according to an embodiment of the present invention.

The results are shown in FIG. 15.

As seen from FIG. 15, it was confirmed that melanin was statistically significantly decreased in the group treated with a mixture of Compound 1 and Compound 2, as compared with the control group. In addition, it was confirmed that the melanin amount ascending to the stratum corneum was 43.25% and statistically significantly decreased as compared with the control group.

From the above-described results, it was confirmed that the compound according to embodiments of the present invention may effectively induce melanosome degradation by autophagy activation and also promote PAR-2 inhibition to effectively inhibit transfer of melanosomes.

Specifically, Compound 1 which is a melanosome degradation inducing compound by autophagy activation induces autophagy activation of melanocytes to effectively degrade melanosomes, and Compound 2 which is a melanosome transfer inhibition inducing compound by endocytosis inhibition has an excellent effect on the interference of entry of melanosomes to keratinocytes. Thus, melanin in keratinocytes was eventually decreased, and thus, it is expected that Compound 1 and Compound may be used for alleviating, treating, and preventing skin pigmentation very effectively. In particular, when the compounds represented by Chemical Formula 2 and Chemical Formula 3 according to embodiments of the present invention are mixed for use, an excellent effect on improvement, prevention, and treatment of a disorder by melanin hyperpigmentation, as well as a whitening effect may be implemented.

(Examples 13 and 14 and Comparative Example 1) Production of Cosmetic Composition for Whitening The contents of the components listed in the following Table 2 were added to an emulsification reactor and heated to ° C. while mixing and stirring, thereby being emulsified. Thereafter, when emulsification was completed, stirring was carried out with a stirrer and slow cooling to room temperature was carried out, thereby producing a cosmetic composition for whitening (o/w cream).

TABLE 2

| Components | | Content (wt %) | | |
|---|---|---|---|---|
| | | Comparative Example 1 | Example 13 | Example 14 |
| Effective | Compound 1 | — | 0.000625 | 0.0025 |
| component | Compound 2 | — | 0.001875 | 0.0075 |
| Stearic acid | | 3.0 | 3.0 | 3.0 |
| Allantoin | | 0.1 | 0.1 | 0.1 |
| Glycerin | | 10 | 10 | 10 |
| Methylgluceth-20 | | 2 | 2 | 2 |
| Cetearyl alcohol | | 2 | 2 | 2 |
| Glyceryl stearate | | 1 | 1 | 1 |
| Ceteth-20 | | 2 | 2 | 2 |
| Caprylic/capric triglyceride | | 5 | 5 | 5 |
| Cyclopentasiloxane | | 5 | 5 | 5 |
| Shea butter | | 5 | 5 | 5 |
| Tocopheryl acetate | | 0.5 | 0.5 | 0.5 |
| Sodium acrylate/sodium acryloyldimethyl taurate copolymer | | 2 | 2 | 2 |
| Snail secretion filtrate | | 6 | 6 | 6 |
| Rosa centifolia flower water | | 5 | 5 | 5 |
| Caprylhydroxamic acid/caprylylglycol/ glycerin | | 1 | 1 | 1 |
| Purified water | | Residual amount | Residual amount | Residual amount |

(Example 15) Whitening Effect

In order to investigate the whitening effect of the cosmetic composition for whitening of the Examples prepared by the above method, a clinical test was performed.

As a specific experimental method, the skin of 20 adult men and women (15 women and 5 men) of an average age of 37 (36.57±5.90) suffering from hyperpigmentation was exposed to UV to induce blackening, and creams containing Compound 1 and Compound 2 at a high concentration and at a low concentration (test samples) as listed in Table 2 and a cream which does not contain Compound 1 and Compound 2 (Comparative Example 1, control sample) were applied thereon twice a day. 4 weeks and 8 weeks after each cream was applied, measurement was performed according to the device manual using Mexameter and Chromameter, and for the measurement values, after a test of normality, ANOVA was performed for a change over evaluation time and significance between before/after sample application and test sample/control sample for each week was confirmed with a difference in hypothesized mean of 5% (P<0.05) by a paired t-test. As a statistical analysis program, IBM SPSS version 18.0 was used.

The results are shown in the following Tables 3 and 4.

TABLE 3

| Change in melanin | Before experiment | After 4 weeks (improvement rate) | After 8 weeks (improvement rate) |
|---|---|---|---|
| Comparative Example 1 | 212.75 + 55.86 | 201.70 + 58.83 (5.19%) | 159.00 + 36.69 (25.26%) |
| Example 13 | 212.10 + 53.99 | 196.80 + 58.68 (7.21%) | 153.71 + 35.71 (27.53%) |
| Example 14 | 213.85 + 55.73 | 194.80 + 54.04 (8.91%) | 150.80 + 34.63 (29.48%) |

TABLE 4

| Change in skin brightness | Before experiment | After 4 weeks (improvement rate) | After 8 weeks (improvement rate) |
|---|---|---|---|
| Comparative Example 1 | 70.37 + 2.92 | 72.55 + 2.20 (3.00%) | 74.00 + 1.94 (5.16%) |
| Example 13 | 70.66 + 3.07 | 74.63 + 2.60 (5.62%) | 76.82 + 2.17 (8.72%) |
| Example 14 | 69.46 + 3.51 | 75.23 + 2.26 (8.31%) | 77.83 + 2.15 (12.01%) |

As seen from Tables 3 and 4, it was confirmed that changes in melanin pigmentation and skin brightness were improved in a group using a cosmetic composition including the melanosome degradation inducing compound by autophagy activation and the melanosome transfer inhibition inducing compound by endocytosis inhibition according to embodiments of the present invention. In addition, it was confirmed that the improvement rates of changes in melanin pigmentation and skin brightness expressed more improved effects as the use time passed.

The compound according to embodiments of the present invention or the pharmaceutically acceptable salt thereof may increase expression of autophagy-related proteins to activate autophagy and protect cells from oxidation stress. In addition, the compound according to embodiments of the present invention or the pharmaceutically acceptable salt thereof may improve, prevent, or treat various diseases and phenomena caused by oxidation stress. In particular, the compound according to embodiments of the present invention or the pharmaceutically acceptable salt thereof has a merit of inducing melanosome degradation, thereby allowing implementation of a surprising whitening effect by autophagy activation which decreases melanin production.

The compound according to embodiments of the present invention or the pharmaceutically acceptable salt thereof induces melanosome degradation to decrease melanin pigmentation and also effectively inhibits endocytosis into keratinocytes to prevent transfer of melanosomes. That is, the compound according to embodiments of the present invention or the pharmaceutically acceptable salt thereof is very effective for improving, preventing, or treating a hyperpigmentation disorder induced from melanin.

Hereinabove, although the present invention has been described by specified matters and specific embodiments, they have been provided only for assisting in the entire understanding of the present invention, and the present invention is not limited to the embodiments. Various modifications and changes may be made by those skilled in the art to which the present invention pertains from this description.

Therefore, the spirit of the present invention should not be limited to the above-described embodiments, and the following claims as well as all modified equally or equivalently to the claims are intended to fall within the scope and spirit of the invention.

What is claimed is:

1. A compound represented by the following Chemical Formula 1 or a pharmaceutically acceptable salt thereof:

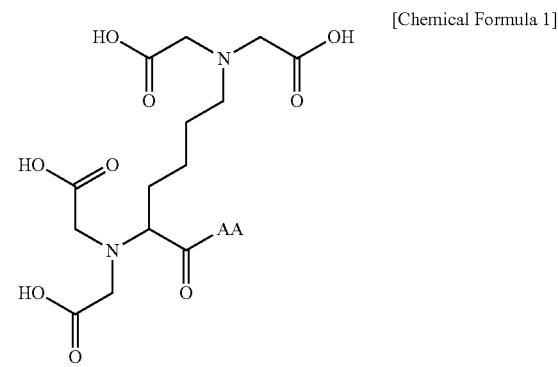

[Chemical Formula 1]

wherein AA is an amino acid residue containing unsubstituted or substituted proline.

2. The compound or the pharmaceutically acceptable salt thereof of claim 1, wherein AA is an amino acid residue containing proline which is unsubstituted or substituted with one or more substituents selected from the group consisting of hydroxy, $C_{1-10}$ alkoxy, $C_{1-10}$ alkylcarbonyl, and carboxy.

3. The compound or the pharmaceutically acceptable salt thereof of claim 1, wherein the compound represented by Chemical Formula 1 or the pharmaceutically acceptable salt thereof is a compound represented by the following Chemical Formula 2 or a pharmaceutically acceptable salt thereof:

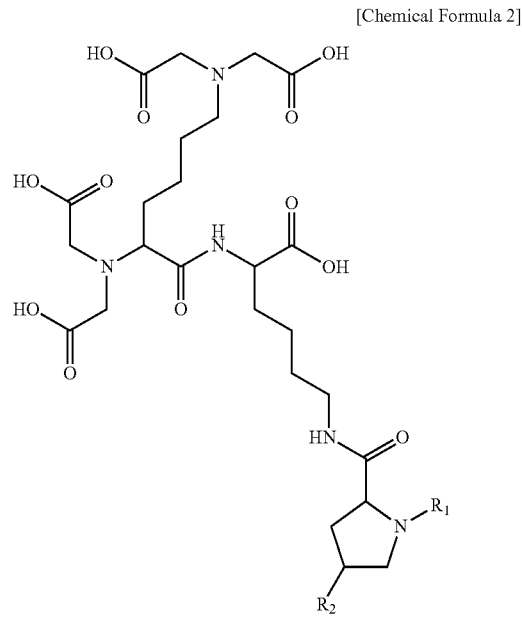

[Chemical Formula 2]

wherein

R$_1$ is C$_{1-10}$ alkylcarbonyl; and

R$_2$ is hydrogen, hydroxy, C$_{1-10}$ alkoxy, C$_{1-10}$ alkylcarbonyl, or carboxy.

4. The compound or the pharmaceutically acceptable salt thereof of claim 1, wherein the compound represented by Chemical Formula 1 or the pharmaceutically acceptable salt thereof is a compound represented by the following Chemical Formula 3 or a pharmaceutically acceptable salt thereof:

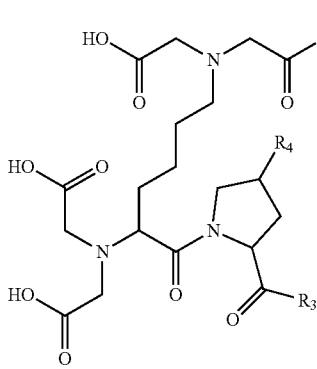

[Chemical Formula 3]

wherein

R$_3$ is hydroxy or C$_{1-10}$ alkyl; and

R$_4$ is hydrogen, hydroxy, C$_{1-10}$ alkoxy, C$_{1-10}$ alkylcarbonyl, or carboxy.

5. A composition comprising: at least one ft compound represented by the following Chemical Formula 1 and/or at least one pharmaceutically acceptable salt thereof as an effective component:

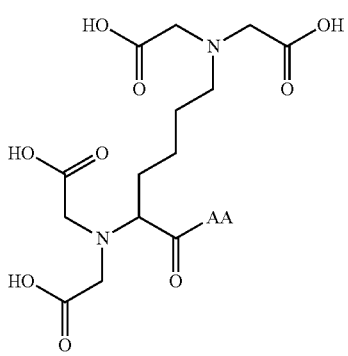

[Chemical Formula 1]

wherein AA is an amino acid residue containing unsubstituted or substituted proline.

6. The composition of claim 5, wherein the effective component comprises a compound represented by the following Chemical Formula 2 or a pharmaceutically acceptable salt thereof:

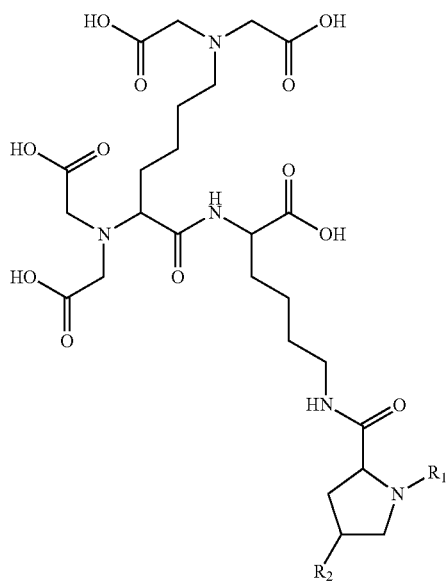

[Chemical Formula 2]

wherein

R$_1$ is C$_{1-10}$ alkylcarbonyl; and

R$_2$ is hydrogen, hydroxy, C$_{1-10}$ alkoxy, C$_{1-10}$ alkylcarbonyl, or carboxy.

7. The composition of claim 5, wherein the effective component comprises a compound represented by the following Chemical Formula 3 or a pharmaceutically acceptable salt thereof:

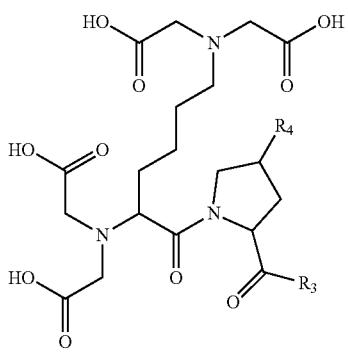

[Chemical Formula 3]

wherein

R$_3$ is hydroxy or C$_{1-10}$ alkyl; and

R$_4$ is hydrogen, hydroxy, C$_{1-10}$ alkoxy, C$_{1-10}$ alkylcarbonyl, or carboxy.

8. The composition of claim 5, wherein the effective component comprises:

a compound represented by the following Chemical Formula 2 or a pharmaceutically acceptable salt thereof (A) and a compound represented by the following Chemical Formula 3 or a pharmaceutically acceptable salt thereof (B):

[Chemical Formula 2]

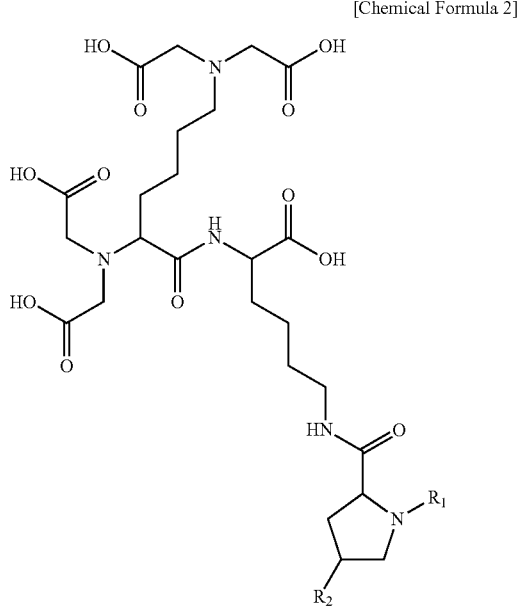

[Chemical Formula 3]

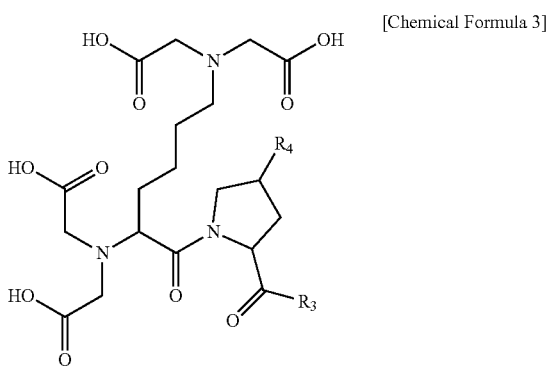

wherein

R₁ is $C_{1-10}$ alkylcarbonyl;

R₃ is hydroxy or $C_{1-10}$ alkyl; and

R₂ and R₄ are independently of each other hydrogen, hydroxy, $C_{1-10}$ alkoxy, $C_{1-10}$ alkylcarbonyl, or carboxy.

9. The composition of claim 8, wherein the effective component comprises A and B at a weight ratio (A:B) of 1:0.1 to 1:1.

10. The composition of claim 5, wherein the composition includes 0.0001 to 10 wt % of the effective component, based on a total weight of the composition.

11. A method for improving or treating a melanin hyperpigmentation disorder, the method comprising:
   administering an effective amount of the composition of claim 5 to a subject in need of such improvement or treatment.

12. A method for improving or treating a melanin hyperpigmentation disorder, the method comprising:
   administering an effective amount of the composition of claim 6 to a subject in need of such improvement or treatment.

13. A method for improving or treating a melanin hyperpigmentation disorder, the method comprising:
   administering an effective amount of the composition of claim 7 to a subject in need of such improvement or treatment.

14. A method for improving or treating a melanin hyperpigmentation disorder, the method comprising:
   administering an effective amount of the composition of claim 8 to a subject in need of such improvement or treatment.

15. The method of claim 14, wherein the effective component comprises A and B at a weight ratio (A:B) of 1:0.1 to 1:1.

16. The method of claim 11, wherein the melanin hyperpigmentation disorder is freckles, senile plaque, liver spots, chloasma, brown or black spots, sunlight pigmented spots, cyanic melasma, hyperpigmentation after using drugs, chloasma gravidarum, or hyperpigmentation after inflammation.

17. The method of claim 11, wherein the composition includes 0.0001 to 10 wt % of the effective component, based on a total weight of the composition.

18. A method of skin whitening, comprising:
   applying the composition of claim 5 onto skin in need of whitening.

19. A method of skin whitening, comprising:
   applying the composition of claim 6 onto skin in need of whitening.

20. A method of skin whitening, comprising:
   applying the composition of claim 7 onto skin in need of whitening.

21. A method of skin whitening, comprising:
   applying the composition of claim 8 onto skin in need of whitening.

* * * * *